United States Patent
Morgan et al.

(10) Patent No.: US 6,903,074 B1
(45) Date of Patent: Jun. 7, 2005

(54) NEUROMEDIN B AND SOMATOSTATIN RECEPTOR AGONISTS

(75) Inventors: Barry A. Morgan, Franklin, MA (US); Dean Sadat-Aalaee, Marina Del Ray, CA (US)

(73) Assignee: Societe de Conseils de Recherches et d'Applications Scientifiques, S.A.S., Paris (FR)

(*) Notice: Subject to any disclaimer, the term of this patent is extended or adjusted under 35 U.S.C. 154(b) by 338 days.

(21) Appl. No.: 09/980,133

(22) PCT Filed: Jun. 5, 2000

(86) PCT No.: PCT/US00/15396
§ 371 (c)(1),
(2), (4) Date: Feb. 22, 2002

(87) PCT Pub. No.: WO00/75186
PCT Pub. Date: Dec. 14, 2000

Related U.S. Application Data

(60) Provisional application No. 60/137,655, filed on Jun. 4, 1999.

(51) Int. Cl.[7] .............................. A61K 38/08; C07K 7/06
(52) U.S. Cl. .............................. 514/15; 514/16; 514/17; 530/311; 530/321; 530/328
(58) Field of Search ................................ 530/311, 321; 530/328; 514/15, 16, 17

(56) References Cited

U.S. PATENT DOCUMENTS 5,462,926 A  10/1995  Coy et al. ..................... 514/16

FOREIGN PATENT DOCUMENTS

| EP | 0 127 899 | 6/1984 |
|---|---|---|
| EP | 0 395 417 A1 | 4/1990 |
| EP | 0 395 417 B1 | 4/1990 |
| EP | 0 478 101 A2 | 9/1991 |
| EP | 1 033 372 A1 | 11/1998 |
| JP | WO 99/25729 | 5/1999 |
| WO | WO 84/04916 | 12/1984 |
| WO | WO 93/03056 | 2/1993 |
| WO | WO 94/05310 | 3/1994 |
| WO | WO 97/11962 | 4/1997 |
| WO | WO 98/51332 | 11/1998 |

OTHER PUBLICATIONS

David H. Coy, et al., "Somatostatin receptor antagonists based on a mixed neuromedin B antagonist/somatostatin agonist" Pept. Proc. Am. Pept. Symp., 15th (1999), pp. 526–529, XP000917964.

Richard R. Ryan et al., "Comparative Pharmacology of the Nonpeptide Neuromedin B Receptor Antagonist PD 168368" J. Pharmacol. Exp Ther. (1999), pp. 1202–1211, XP000917708.

Akira Kubota et al., "Effector Coupling of Somatostatin Receptor Subtypes on Human Endocrine Tumors", Metabolism Clinical and Experimental, (1996), vol. 45, no 8 Suppl. 1, pp. 42–45 XP002149617.

A. Horvàth et al., "Somatostatin Octa– and Heptapeptides, Structural and Biological Characteristics", Pept. (1998), Proc. Eur. Pept. Symp, pp. 483–484, XP000918406.

*Primary Examiner*—Robert A. Wax
(74) *Attorney, Agent, or Firm*—Fish & Richardson; Brian R. Morrill; Alan F. Feeney

(57) ABSTRACT

A novel class of analogs which exhibit both high affinity and selectivity for Neuromedin B and Somatostann receptors are claimed. One example is Nal-Tyr-cyclo(D-Cys-D-Trp-Lys-D-Cys)-Abu-Nal-NH$_2$.

25 Claims, No Drawings

NEUROMEDIN B AND SOMATOSTATIN RECEPTOR AGONISTS

This application claims benefit of Ser. No. 60/137,655, filed Jun. 4, 1999.

BACKGROUND OF THE INVENTION

The mammalian bombesin (Bn)-related peptides, gastrin-releasing peptide (GRP) and neuromedin B (NMB) have a wide range of biological and pharmacological effects. These include stimulation of the release of numerous gastrointestinal hormones and peptides, stimulation of exocrine gland secretion chemotaxis, contraction of smooth muscle, effects in the central nervous system such as thermoregulabon, behavioral effects, maintenance of circadian rhythm, inhibition of TSH release and safety. Bn-related peptides also function as a growth factor in numerous normal cells (e.g., bronchial cells, endometrial stomal cells and 3T3 cells) as well as neoplastic cells such as human small cell lung cancer cells, rat hepatocellular tumor cells, prostatic cells and breast adenocarcinoma cells.

Recent structure-function and cloning studies demonstrate that at least two classes of receptors mediate the actions of Bn-related peptides. One class, the GRP-preferring subtype (GRP receptor or GRP-R), has a high affinity for GRP and low affinity for NMB, whereas the other class, the NMB-preferring subtype (NMB receptor or NMB-R), has a high affinity for NMB and lower affinity for GRP. Both classes of receptors are widely present both in the central nervous system and in the gastrointestinal tract. Until recently, the physiological importance of Bn-related peptides in mediating various processes or which receptor subtype mediated the various reported biological effects of Bn-related peptides was unclear.

Five different classes of Bn-receptor antagonists have been described. Jensen, R. T. et al. *Trends Pharmacol. Sci.* 12:13 (1991). Members of a number of these classes have high potency, long duration of action and selectivity for the GRP receptor and thus are useful even in vivo for defining the role of GRP or GRP receptors in mediating various physiological events. However, at present few antagonists for the NMB receptor which are sufficiently selective or potent have been described. (See, e.g., Coy, D., and Taylor, J., U.S. Pat. No. 5,462,926.) Further, NMB has been implicated in the inhibition of lung cancer and gliomas, Cancer Res 1991 Oct. 1 51:19 5205–11; J Cell Biochem Suppl 1996 24: 237–46, Peptides 1995 16:6 1133–40; J Pharmacol Exp Ther 1992 October 263:1 311–7), stimulation of appetite, (Eur J Pharmacol 1994 Dec. 12 271:1 R7–9; Am J Physiol 1997 January 272:1 Pt 2 R433–7; Pharmacol Biochem Behav 1996 August 54:4 705–11), stimulation of TSH secretion, (hypothyroidism), (Regul Pept 1996 Nov. 14 67:1 47–53), and inhibition of aldosterone secretion, (hyperaldosteronism), (Histol Histopathol 1996 October 11:4 895–7). Thus, the compounds of the present invention are useful in the investigation of the physiological role played by NMB, and in the development of therapeutic compositions for treatment of NMB-related indications.

As is known in the art, agonists and antagonists of somatostatin are useful for treating a variety of medical conditions and diseases, such as inhibition of *H. pylori* proliferation, acromegaly, restenosis, Crohn's disease, systemic sclerosis, external and internal pancreatic pseudocysts and ascites, ViPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux and in treating endocrinological diseases and/or conditions, such as Cushing's Syndrome, gonadotropinoma, hyperparathyroidism, Graves' Disease, diabetic neuropathy, Paget's disease, and polycystic ovary disease; in treating various types of cancer such as thyroid cancer, hepatome, leukemia, meningioma and conditions associated with cancer such as cancer cachexia; in the treatment of such conditions as hypotension such as orthostatic hypotension and postprandial hypotension and panic attacks; GH secreting adenomas (Acromegaly) and TSH secreting adenomas. Activation of type 2 but not type 5 subtype receptor has been associated with treating prolactin secreting adenomas. Other indications associated with activation of the somatostatin subtypes are inhibition of insulin and/or glucagon and more particularly diabetes mellitus, hyperlipidemia, insulin insensitivity, Syndrome X, angiopathy, proliferative retinopathy, dawn phenomenon and Nephropathy; inhibition of gastric acid secretion and more particularly peptic ulcers, enterocutaneous and pancreaticocutaneous fistula, Dumping syndrome, watery diarrhea syndrome, acute or chronic pancreatitis and gastrointestinal hormone secreting tumors: inhibition of angiogenesis, treatment of inflammatory disorders such as arthritis; chronic allograft rejection; angioplasty; preventing graft vessel and gastrointestinal bleeding. Somatostatin agonists can also be used for decreasing body weight in a patient. Accordingly, the compounds of the instant invention are useful for the foregoing methods.

Recently, it was reported that a native somatostatin (SS), somatostatin-14 (SS-14), inhibited the cross-linking of $^{125}$I-GRP to a 120 kD protein in triton extracts of 3T3 cells and human small cell lung cancer cells which are known to possess bombesin receptors. Recent studies have also demonstrated SS-14 could also weakly inhibit binding to opiate receptors, and subsequent structure-function led to the identification of various D-amino acid-substituted and constrained amino acid-substituted cyclo somatostatin analogs that functioned as potent mu opioid receptor antagonists.

All patents and publications mentioned herein are hereby incorporated by reference in their entirety.

SUMMARY OF THE INVENTION

The present invention relates to a series of analogues having unique structural features, and to a method of selectively modulating biochemical activity of cells induced by somatostatin and/or neuromedin B.

In one aspect the present invention is directed to a compound of the formula (I), (I)

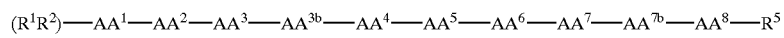

$(R^1R^2)$—$AA^1$—$AA^2$—$AA^3$—$AA^{3b}$—$AA^4$—$AA^5$—$AA^6$—$AA^7$—$AA^{7b}$—$AA^8$—$R^5$ or a pharmaceutically acceptable salt thereof,
wherein
the α-nitrogen of $AA^1$, $AA^2$, $AA^3$, $AA^{3b}$, $AA^4$, $AA^5$, $AA^7$, $AA^{7b}$, and $AA^8$ each is, independently, optionally substituted with $(C_{1-4})$alkyl, $(C_{3-4})$alkenyl, $(C_{3-4})$alkynyl, or $(C_{1-5})$alkyl-C(O)—;

$AA^1$ is absent or the D- or L-isomer of an amino acid selected from the group consisting of $R^{11}$, Aac, Aic, Arg, Asn, Asp, Dip, Gln, Glu, Hca, Hyp, Lys, Mac, Macab, Orn, Pro, Ser, Ser(Bzl), Thr, Thr(Bzl), Pip, hArg, Bip, Bpa, Tic, Cmp, Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, C4c, 5-Iqs, Htqa, 4-Mqc, Thn, α-Chpa, Cit, Nua, Pyp and an optionally substituted aromatic α-amino acid;
  wherein said optionally substituted aromatic α-amino acid is optionally substituted with one or more substituents each independently selected from the group consisting of halogen, $NO_2$, OH, CN, $(C_{1-6})$alkyl, $(C_{2-6})$alkenyl, $(C_{2-6})$alkynyl, $(C_{1-6})$alkoxy, Bzl, O-Bzl, and $NR^9R^{10}$;

$AA^2$ is absent or the D- or L-isomer of an amino acid selected from the group consisting of $R^{11}$, Aic, Arg, Hca, His, Hyp, Pal, $F_5$-Phe, Phe, Pro, Trp, and $X^0$-Phe Pip, hArg, Bip, Bpa, Tic, Cmp Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, 1-Iqc, 3-Iqc, C4c, 5-Iqs, Htqa, 4-Mqc, Thn, α-Chpa, Cit, Nua, and Pyp;

$AA^3$ is the D- or L-isomer of an amino acid selected from the group consisting of Cys, hCys, Pen, Tpa, Tmpa, Mac, Macab, and an optionally substituted aromatic α-amino acid;
wherein said optionally substituted aromatic α-amino acid is optionally substituted with one or more substituents selected from the group consisting of halogen, $NO_2$, OH, CN, $(C_{1-4})$alkyl, $(C_{2-4})$alkenyl, $(C_{2-4})$alkynyl, $(C_{1-4})$alkoxy, Bzl, O-Bzl, $NR^9R^{10}$, Pip, hArg, Bip, Bpa, Tic, Cmp Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, 1-Iqc, 3-Iqc, C4c, 5-Iqs, Htqa, 4-Mqc, Thn, α-Chpa, Cit, Nua, and Pyp; $AA^{3b}$ is absent or the D- or L-isomer of an amino acid selected from the group consisting of Pal, 4-Pal, His, Arg, Nal, Trp, Bpa, $F_5$-Phe, Phe, $X^0$-Phe, $R^{11}$, hArg, Bip, Tic Htic, Dip, Sala, Aala, Thza, Thia, Bal, Fala, and Pala;

$AA^4$ is a D- or L-isomer of an optionally substituted amino acid or of an optionally substituted aromatic α-amino acid;
  wherein said optionally substituted amino acid is selected from the group consisting of Trp, Lys, Orn, hLys, cis-4-Acha, trans-4-Acha, trans-4-Amcha, 4-Pip-Gly, N-Met-Trp, α-Met-Trp, His, hHis, hArg, Bip, Tic, Htic, Dip, Sala, Aala, Thza, Thia, Bal, Fala, Pala, and 4-Pip-Ala;
    wherein the side chain amino group of said optionally substituted amino acid is optionally substituted with $R^3$ and $R^4$; and
  wherein said optionally substituted aromatic α-amino acid is optionally substituted with one or more substituents each independently selected from the group consisting of halogen, $NO_2$, OH, CN, $(C_{1-4})$alkyl, $(C_{2-4})$alkenyl, $(C_{2-4}1)$alkynyl, Bzl, O-Bzl, and $NR^9R^{10}$;

$AA^5$ is absent, $R^{11}$, Aic, A3c, A4c, A5c, A6c, Abu, Aib, β-Ala, Bpa, Cha, Deg, Gaba, Ile, Leu, Nal, Nle, Pro, Sar, Ser, Ser(Bzl), Thr, Thr(Bzl), Trp, Val, Pal, F-Phe, Phe, $X^0$-Phe, or an optionally substituted D- or L-isomer of an amino acid selected from the group consisting of 4-Pip-Gly, 4-Pip-Ala, cis-4-Acha, trans-4-Acha, trans-4-Amcha, hLys, Lys, Orn, hArg, Bip, Tic, Htic, Dip, Sala, Aala, Thza, Thia, Bal, Fala, and Pala; wherein the side-chain amino group of said optionally substituted amino acid is optionally mono- or di-substituted with $R^3$ and $R^4$;

$AA^6$ is absent or the D- or L-isomer of an amino acid selected from the group consisting of $R^{11}$, an optionally substituted aromatic α-amino acid, Cys, hCys, Pen, Tpa, Tmpa, Thr, Thr(Bzl), Ser, Ser(Bzl), hArg, Bip, Tic, Htic, Dip, Sala, Aala, Thza, Thia, Bal, Fala, and Pala;

$AA^7$ is absent or the D- or L-isomer of an amino acid selected from the group consisting of $R^{11}$, an optionally substituted aromatic α-amino acid, A3c, A4c, A5c, A6c, Abu, Aib, Aic, β-Ala, Arg, Cha, Deg, Gaba, Ile, Leu, Nle, Pip, Pro, Sar, Ser, Ser(Bzl), Thr, Thr(Bzl), Val, Tic, Htic, Sala, Aala, Thza, Thia, Bal, Fala, Pala, hArg, Bip, Bpa, Dip, Pal, Sala, and $X^0$-Phe;

$AA^{7b}$ is absent or a D- or L-isomer of an amino acid selected from the group consisting of $R^{11}$, Bpa, Phe, $F_5$-Phe, $X^0$-Phe, Nal, Pro, Ser, Ser(Bzl), Thr, Thr(Bzl), Trp, hArg, Bip, Tic, Htic, Dip, Sala, Aala, Thza, Thia, Bal, Fala, and Pala;

$AA^8$ is absent or the D- or L- isomer of an amino acid selected from the group consisting of $R^{11}$, Maa, Maaab, Thr, Thr(Bzl), Ser, Ser(Bzl), Tyr, Phe(4-O-Bzl), $F_5$-Phe, and $X^5$-Phe, and an optionally substituted aromatic α-amino acid;

$R^1$ and $R^2$ each is, independently, H, E—, $E(O)_2S$—, E(O)C—, EOOC—, $R^{13}$, or absent;

$R^3$ and $R^4$ each is, independently, $(C_{1-12})$alkyl, $(C_{2-12})$alkenyl, $(C_{2-12})$alkynyl, phenyl, naphthyl, phenyl-$(C_{1-6}$ alkyl, phenyl-$(C_{2-6})$alkenyl, phenyl-$(C_{2-6})$alkynyl, naphthyl-$(C_{1-6})$alkyl, naphthyl-$(C_{2-6})$alkenyl, naphthyl-$(C_{2-6})$alkynyl, (cyclo$(C_{3-7})$alkyl)-$(C_{1-6})$alkyl, (cyclo$(C_{3-7})$alkyl)-$(C_{2-6})$alkenyl, (cyclo$(C_{3-7})$alkyl)-$(C_{2-6})$alkynyl, heterocyclyl-$(C_{1-4})$alkyl, heterocyclyl-$(C_{2-4})$alkenyl, heterocyclyl)-$(C_{2-4})$alkynyl, 1-adamantyl, 2-adamantyl, 9-fluorenylmethyl, dicyclopropylmethyl, dimethylcyclopropylmethyl, or benzhydryl;

$R^5$ is —$OR^6$, —$NR^7R^8$, or absent,
  wherein each $R^6$, $R^7$ and $R^8$ is, independently, H, $(C_{1-12})$alkyl, $(C_{2-12})$alkenyl, $(C_{2-12})$alkynyl, phenyl, naphthyl, phenyl-$(C_{1-6})$alkyl, phenyl-$(C_{2-6})$alkenyl, phenyl-$(C_{2-6})$alkynyl, naphthyl-$(C_{1-6})$alkyl, naphthyl-$(C_{2-6})$alkenyl, naphthyl-$(C_{2-6})$alkynyl, 1-adamantyl, 2-adamantyl, 9-fluorenylmethyl, dicyclopropylmethyl, dimethylcyclopropylmethyl, or benzhydryl;

$R^9$ and $R^{10}$ each is, independently, H, $(C_{1-6})$alkyl, $(C_{3-4})$alkenyl, $(C_{3-4})$alkynyl, 1-adamantyl, or 2-adamantyl;

$R^{11}$ is, independently for each occurrence, a D- or L-amino acid of the formula:

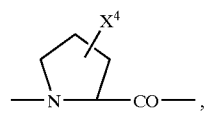

(1)

-continued

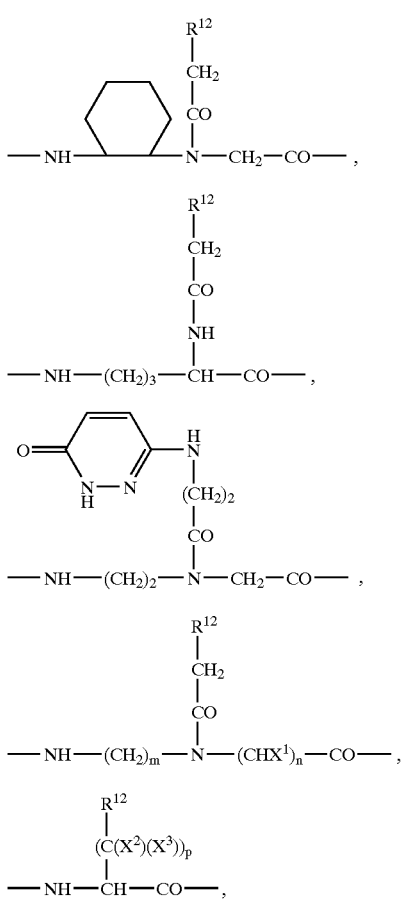

(2)

(3)

(4)

(5)

(6)

wherein m and n each is, independently, 1, 2, or 3, and p is 0, 1, or 2;

$R^{12}$ is, independently for each occurrence, an optionally substituted moiety of the formula:

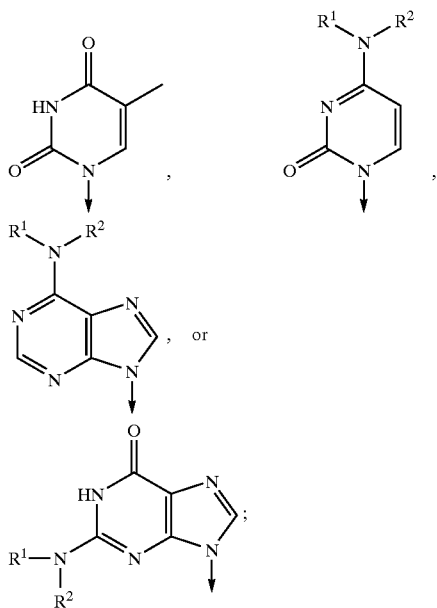

$R^{13}$ is a moiety of the formula

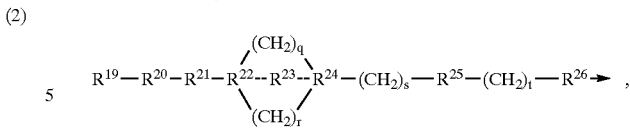

wherein q, r, s, and t each is, independently, 0, 1, 2, 3, 4 or 5;

$R^{19}$ is absent, H, $NH_2$, OH, $(C_{1-6})$hydroxyalkyl, $N(R^{27}R^{28})$, $SO_3H$, or an optionally substituted moiety selected from the group consisting of heterocyclyl, phenyl and naphthyl,
wherein the optionally substituted moiety defined for $R^{19}$ is optionally substituted with one or more substituents selected, independently for each occurrence, from the group consisting of halogen, $NO_2$, OH, $(C_{1-6})$alkyl, $(C_{2-6})$alkenyl, $(C_{2-6})$alkynyl, $(C_{1-6})$alkoxy, $NH_2$, mono- or di-$(C_{1-6})$alkylamino, Bzl, and O-Bzl;

$R^{20}$ is O or absent;
$R^{21}$ is $(C_{1-6})$alkyl or absent;
$R^{22}$ is N, O, C, or CH;
$R^{23}$ is $(C_{1-6})$alkyl or absent,
$R^{24}$ is N, CH, or C;
$R^{25}$ is NH, O, or absent;
$R^{26}$ is $SO_2$, CO, or CH;
$R^{27}$ and $R^{28}$ each is, independently, H or $(C_{1-6})$alkyl;

E is, independently for each occurrence, an optionally substituted moiety selected from the group consisting of $(C_{1-12})$alkyl, $(C_{2-12})$alkenyl, $(C_{2-12})$alkynyl, phenyl, naphthyl, phenyl-$(C_{1-6})$alkyl, phenyl-$(C_{2-6})$alkenyl, phenyl-$(C_{2-6})$alkynyl, naphthyl-$(C_{1-6})$alkyl, naphthyl-$C_{2-6})$alkenyl, naphthyl-$(C_{2-6})$alkynyl, (cyclo$(C_{3-6})$alkyl)-$(C_{1-6})$alkyl, (cyclo$(C_{3-7})$alkyl)-$(C_{2-6})$alkenyl, (cyclo$(C_{3-7})$alkyl)-$(C_{2-4})$alkynyl, heterocyclyl-$(C_{1-4})$alkyl, heterocyclyl-$(C_{2-4})$alkenyl, heterocyclyl-$(C_{2-4})$alkynyl, 1-adamantyl, 2-adamantyl, dicyclopropylmethyl, dimethylcyclopropylmethyl, 9-fluorenylmethyl, and benzhydryl;
wherein the optionally substituted moiety defined for E is optionally substituted with one or more substituents each independently selected from the group consisting of halogen, OH, Bzl, O-Bzl, $NO_2$, CN, COOH, and SH;

$X^0$ is halogen, $NO_2$, OH, $(C_{1-6})$alkyl, $(C_{1-6})$alkoxy, mono- or di-$(C_{1-6})$alkylamino, Bzl, O-Bzl, $NR^9R^{10}$, or CN;

$X^1$ is H, $(C_{1-6})$alkyl, $(C_{2-6})$alkenyl, $(C_{2-6})$alkynyl, indolyl, imidazolyl, 1-naphthyl, 3-pyridyl, optionally ring-substituted benzyl, or a moiety which corresponds to the side-chain group of Arg, Leu, Gln, Lys, Tyr, His, Thr, Trp, Phe, Val, Ala, Lys, or His;
wherein said optionally ring-substituted benzyl is optionally substituted with one or more substituents selected from the group consisting of halogen, OH, $(C_{1-6})$ alkoxy, mono- or di-$(C_{1-6})$alkylamino, $(C_{1-4})$alkyl, $(C_{2-4})$ alkenyl, $(C_{2-4})$alkynyl, and $NR^9R^{10}$;

$X^2$ and $X^3$ each is, independently, H, halogen, OH, =O, =S, $(C_{1-12})$alkyl, $(C_{2-12})$alkenyl, $(C_{2-12})$alkynyl, phenyl, naphthyl, phenyl-$(C_{1-6})$alkyl, phenyl-$(C_{2-6})$alkenyl, phenyl-$(C_{2-6})$alkynyl, naphthyl-$C_{1-6})$alkyl, naphthyl-$(C_{2-6})$alkenyl, naphthyl-$(C_{2-6})$alkynyl, (cyclo$(C_{3-7})$alkyl)-$(C_{1-6})$alkyl, (cyclo$(C_{3-7})$alkyl)-$(C_{2-5})$alkenyl, (cyclo$(C_{3-7})$ alkyl)-$(C_{2-6})$alkynyl, heterocyclyl-$(C_{1-4})$alkyl, heterocyclyl-$(C_{2-4})$alkenyl, heterocyclyl-$(C_{2-4})$alkynyl, 1-adamantyl, 2-adamantyl, dicyclopropylmethyl, or dimethylcyclopropyl methyl;

$X^4$ is H, OH, or $NH_2$; and
$X^5$ is halogen, $NO_2$, $CH_3$, OH, Bzl or O-Bzl;

provided that at least six amino acid residues are present;

when AA³ is a D- or L-isomer of an amino acid selected from the group consisting of Cys, hCys, Pen, Tpa, or Tmpa, and AA⁶ is a D- or L-isomer of an amino acid selected from the group consisting of Cys, hCys, Pen, Tpa, or Tmpa, then AA³ and AA⁶ are connected by a disulfide bond;

when AA¹ or AA³ is a D- or L-isomer of an amino acid selected from the group consisting of Mac or Macab, then AA⁸ is a D- or L-isomer of an amino acid selected from the group consisting of Maa and Maaab, and when AA⁸ is a D- or L-isomer of an amino acid selected from the group consisting of Maa and Maaab, then AA¹ or AA³ is a D- or L-isomer of Mac or of Macab, and AA¹ or AA³ is connected by a disulfide bond with AA⁸;

AA² can be D- or L-Hca only when AA¹ is absent;

when one of R¹ or R² is E(O)₂S—, E(O)C—, EOOC—, or R¹³, the other is H;

when R⁵ is absent, then one of R¹ or R² is also absent, and the N-terminal amino acid and C-terminal amino acid together form an amide bond;

when one of X² or X³ is C=O or C=S, the other is absent; and said compound of formula (I) is not of the formula:
D-Phe-Tyr-cyclo(D-Cys-D-Trp-Lys-Cys)-Abu-Thr-NH₂;
Ac-Phe-Tyr-cyclo(D-Cys-D-Trp-Lys-Cys)-Abu-Thr-NH₂;
L-4-NO₂-Phe-Tyr-cyclo(D-Cys-D-Trp-Lys-Cys)-Abu-Thr-NH₂;
Ac-L-4-NO₂-Phe-Tyr-cyclo(D-Cys-D-Trp-Lys-Cys)-Abu-Thr-N H₂;
Hca-Tyr-cyclo(D-Cys-D-Trp-Lys-Cys)-Abu-Thr-NH₂;
D-Dip-Tyr-cyclo(Cys-D-Trp-Lys-D-Cys)-Val-Nal-NH₂;
D-4-NO₂-Phe-Phe(4-O-Bzl)cyclo(D-Cys-D-Trp-Lys-Cys) Cha-Nal-NH₂; or
D4-NO₂-Phe-cyclo(D-Cys-Phe(4-O-Bzl)-D-Trp-Lys-Cys)-Val-Tyr-NH₂.

In another aspect, this invention is directed to a pharmaceutical composition comprising one or more of a compound of formula (I), as defined hereinabove, and a pharmaceutically acceptable carrier.

In yet another aspect, the present invention is directed to a method of eliciting an agonist effect from one or more of a somatostatin and/or neuromedin B subtype receptor in a subject in need thereof, which comprises administering a compound of formula (1), as described hereinabove, to said subject.

In still another aspect, the present invention is directed to a method of eliciting an antagonist effect from one or more of a somatostatin and/or neuromedin B subtype receptor in a subject in need thereof, which comprises administering a compound of formula (I), as described hereinabove, to said subject.

In a further aspect, the present invention is directed to a method of binding one or more somatostatin and/or neuromedin B subtype receptor in a subject in need thereof, which comprises administering a compound of formula (I), as described hereinabove, to said subject.

In a still further aspect, the present invention is directed to the use of one or more compounds according to formula I to bind to the neuromedin B receptor or to one or more of the somatostatin receptors, as when performing an in vitro or in vivo assay.

DETAILED DESCRIPTION OF THE INVENTION

One of ordinary skill will recognize that certain substituents listed in this invention may have reduced chemical stability when combined with one another or with heteroatoms in the compounds. Such compounds with reduced chemical stability are not preferred.

In general, the compounds of formula (I) can be made by processes which include processes known in the chemical arts for the production of compounds. Certain processes for the manufacture of formula (I) compounds are provided as further features of the invention and are illustrated by the reaction schemes and examples included herein.

In the above structural formulas and throughout the instant application, the following terms have the indicated meanings unless expressly stated otherwise:

The term alkyl is intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl and the like. When the term $C_0$-alkyl is included in a definition it is intended to denote a single covalent bond.

The term alkoxy is intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term halogen or halo is intended to include the halogen atoms fluorine, chlorine, bromine and iodine.

The term cycloalkyl is intended to include a monocycloalkyl group or a bi-cycloalkyl group of the indicated carbon number known to those of skill in the art.

The term dimethylcyclopropylmethyl refers to the structure

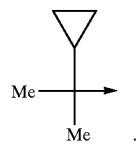

The term aryl is intended to include aromatic rings known in the art, which can be mono-cyclic, bi-cyclic or tri-cyclic, such as phenyl, naphthyl and anthracyl.

The term heterocycle includes mono-cyclic and bi-cyclic systems having one or more heteroatoms, such as oxygen, nitrogen and/or sulfur. The ring systems may be aromatic, for example pyridine, indole, quinoline, pyrimidine, thiophene (also known as thienyl), furan, benzothiophene, tetrazole, dihydroindole, indazole, N-formylindole, benzimidazole, thiazole, and thiadiazole. The ring systems also may be non-aromatic, for example pyrrolidine, piperidine, morpholine and the like.

The chemist of ordinary skill will recognize that certain combinations of heteroatom-containing substituents listed in this invention define compounds which will be less stable under physiological conditions. Accordingly, such compounds are less preferred.

As defined herein, certain residues or moieties are alternatively absent from certain peptides of the invention. Where the bond(s) to such a residue or moiety is indicated by a solid line it is understood that when the residue or moiety is absent a bond is formed between the remaining N-terminal residue or moiety(-ies) and the remaining C-terminal residue or moiety(-ies). Where the bond(s) to such a residue or moiety is indicated by dashed line(s) it is understood that when the residue or moiety is absent no bond is formed between the remaining N-terminal residue or moiety(-ies) and the remaining C-terminal residue or moiety (-ies). For example, in the following structure:

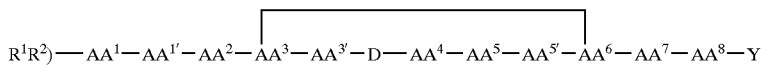

the absence of AA$^1$ results in

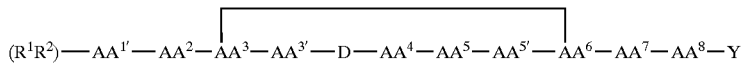

and the absence of AA$^1$ results in

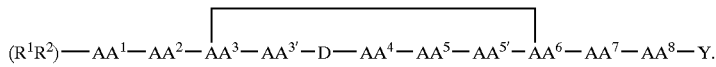

In the following structure:

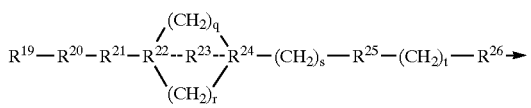

the absence of R$^{23}$ results in

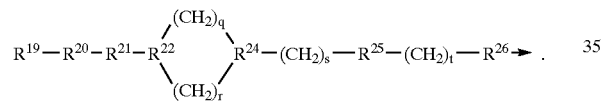

When a chemical structure as used herein has an arrow emanating from it, the arrow indicates the point of attachment For example, the structure

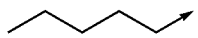

is a pentyl group. When a line is drawn through a cyclic moiety, the line indicates that the substituent can be attached to the cyclic moiety at any of the available bonding points. For example,

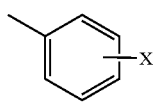

means that the substituent "X" can be bonded ortho, meta or para to the point of attachment. Similarly, when a line is drawn through a bi-cyclic or a tri-cyclic moiety, the line indicates that the substituent can be attached to the bicyclic or a tri-cyclic moiety at any of the available bonding points in any of the rings.

For all formulas depicted herein the N-terminus is at the left and the C-terminus at the right in accordance with the conventional representation of a polypeptide chain.

The symbol AA$^1$, AA$^2$, or the like in a peptide sequence stands for an amino acid residue, i.e., =N—CH(R)—CO— when it is at the N-terminus or —NH—CH(R)—CO— when it is not at the N-terminus, where R denotes the side-chain of that amino acid residue. Thus, R is —CH(CH$_3$)$_2$ for Val. Also, when the amino acid residue is optically active, it is the L-form configuration that is intended unless D-form is expressly designated.

Unless otherwise indicated, where an acetyl group appears at the N-terminus it is understood that the acetyl group is attached to the α-nitrogen rather than to the side chain of the N-terminal amino acid. For example, the structure of the amino acid sequence Ac4-NO$_2$-Phe-AA$^2$-AA$^3$- . . . is:

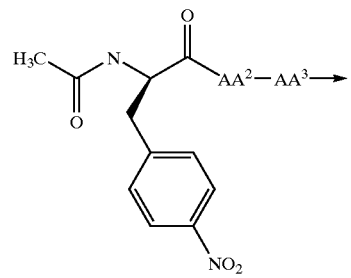

Where the substituent Y appears as, e.g., —OR$^5$, at the C-terminus of the peptide, it is to be understood that —OR$^5$ is attached directly to the carbonyl carbon in replacement of the —OH group.

E(O)C— stands for

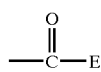

and EOOC— stands for

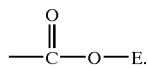

What is meant by "aromatic α-amino acid" is an amino acid residue of the formula

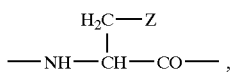

where Z is a moiety containing an aromatic ring. Examples of Z include, but are not limited to, a benzene or pyridine ring and the following structures with or without one or more substituent X on the aromatic ring (where X is, independently for each occurrence, halogen, $NO_2$, $CH_3$, OH, Bzl, or O-Bzl):

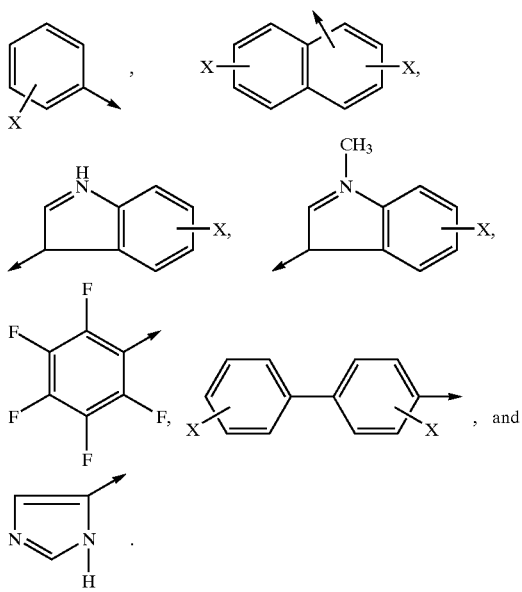

Other examples of an aromatic α-amino acid of the invention are substituted His, such as MeHis, His (τ-Me), or His (π-Me).

What is meant by nucleic acid base is an optionally substituted nucleic acid moiety of the formula:

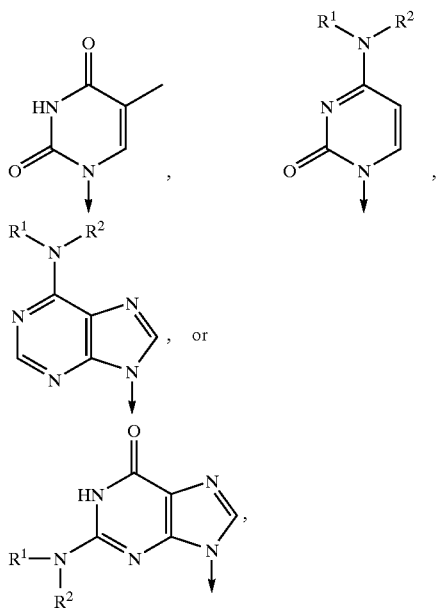

where $R^1$ and $R^2$ are as defined in the claims.

In certain embodiments of the invention the side chain amino group of one or more amino acids is optionally mono- or di-substituted with $R^3$ and $R^4$. For example, substituting $R^3$ onto the side chain amino group of 4-Pip-Gly would result in the following structure:

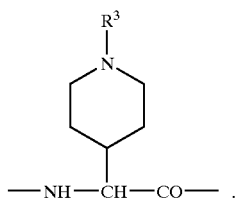

The compounds of the instant invention have at least one asymmetric center. Additional asymmetric centers may be present on the molecule depending upon the nature of the various substituents on the molecule. Each such asymmetric center will produce two optical isomers and it is intended that all such optical isomers, as separated, pure or partially purified optical isomers, racemic mixtures or diastereomeric mixtures thereof, be included within the scope of the instant invention.

The instant compounds can be generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of formula (I) and contacting it with about 1 equivalent of the appropriate corresponding acid of the salt which is desired. Work-up and isolation of the resulting salt is well-known to those of ordinary skill in the art.

The compounds of this invention can be administered by oral, parenteral (e.g., intramuscular, intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration. Accordingly, the present invention includes within its scope pharmaceutical compositions comprising, as an active ingredient, at least one of the compounds of formula (I) in association with a pharmaceutically acceptable carrier.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as coca butter or a suppository wax.

Compositions for nasal or sublingual administration are also prepared with standard excipients well known in the art.

Further, a compound of this invention can be administered in a sustained release composition such as those described in the following patents. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. application Ser. No. 08/929,363 filed Sep. 9, 1997, teaches polymeric sustained release compositions comprising a bioactive agent and chitosan. U.S. application Ser. No. 08/740,778 filed Nov. 1, 1996, teaches sustained release compositions comprising a bioactive agent and cyclodextrin. U.S. application Ser. No. 09/015,394 filed Jan. 29, 1998, teaches absorbable sustained release compositions of a bioactive agent. The teachings of the foregoing patents and applications are incorporated herein by reference.

In general, an effective dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment, all of which are within the realm of knowledge of one of ordinary skill in the art. Generally, dosage levels of between 0.0001 to 100 mg/kg of body weight daily are administered to humans and other animals, e.g., mammals.

A preferred dosage range is 0.01 to 10.0 mg/kg of body weight daily, which can be administered as a single dose or divided into multiple doses, or provided for continuous administration.

Compounds of the instant invention can be and were assessed for their ability to bind to a somatostatin subtype receptor according to the following assays.

The affinity of a compound for human somatostatin subtype receptors 1 to 5 ($sst_1$, $sst_2$, $sst_3$, $sst_4$, and $sst_5$, respectively) is determined by measuring the inhibition of [$^{125}$I-Tyr$^{11}$]SRIF-14 binding to CHO-K1 cells transfected with the sst receptor subtype.

The human sst, receptor gene was cloned as a genomic fragment. A 1.5 Kb Psti-XmnI segment containing 100 bp of the 5'-untranslated region, 1.17 Kb of the entire coding region, and 230 bp of the 3'-untranslated region was modified by the Bg 1II linker addition. The resulting DNA fragment was subcloned into the BamHI site of a pCMV-81 to produce the mammalian expression plasmid (provided by Dr. Graeme Bell, University of Chicago, Chicago, Ill.). A clonal cell line stably expressing the $sst_1$, receptor was obtained by transfection into CHO-K1 cells (American Type Culture Collection, Manassas, Va.) ("ATCC") using the calcium phosphate co-precipitation method. The plasmid pRSV-neo (ATCC) was included as a selectable marker. Clonal cell lines were selected in RPMI 1640 media (Sigma Chemical Co., St. Louis, Mo.) containing 0.5 mg/ml of geneticin (Gibco BRL, Grand Island, N.Y.) ring cloned, and expanded into culture.

The human $sst_2$ somatostatin receptor gene, isolated as a 1.7 Kb BamHI-HindIII genomic DNA fragment and subcloned into the plasmid vector pGEM3Z (Promega), was kindly provided by Dr. G. Bell (University of Chicago, Chicago, Ill.). The mammalian cell expression vector is constructed by inserting the 1.7 Kb BamHI-HindIII fragment into compatible restriction endonuclease sites in the plasmid pCMV5. A clonal cell line is obtained by transfection into CHO-K1 cells using the calcium phosphate co-precipitation method. The plasmid pRSV-neo is included as a selectable marker.

The human $sst_3$ was isolated at genomic fragment, and the complete coding sequence was contained within a 2.4 Kb BamHI/HindIII fragment. The mammalian expression plasmid, pCMV-h3 was constructed by inserting the a 2.0 Kb NcoI-HindIII fragment into the EcoR1 site of the pCMV vector after modification of the ends and addition of EcoR1 linkers. A clonal cell line stably expressing the $sst_3$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_4$ receptor expression plasmid, pCMV-HX was provided by Dr. Graeme Bell (University of Chicago, Chicago, Ill.). The vector contains the 1.4 Kb NheI-NheI genomic fragment encoding the human $sst_4$, 456 bp of the 5'-untranslated region and 200 bp of the 3'-untranslated region, cloned into the XbaI/EcoR1 sites of PCMV-HX. A clonal cell line stably expressing the $sst_4$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

The human $sst_5$ gene was obtained by PCR using a λ genomic clone as a template, and kindly provided by Dr. Graeme Bell (University of Chicago, Chicago, Ill.). The resulting 1.2 Kb PCR fragment contained 21 base pairs of the 5'-untranslated region, the full coding region, and 55 bp of the 3'-untranslated region. The clone was inserted into EcoR1 site of the plasmid pBSSK(+). The insert was recovered as a 1.2 Kb HindIII-XbaI fragment for subcloning into pCVM5 mammalian expression vector. A clonal cell line stably expressing the $SST_5$ receptor was obtained by transfection into CHO-K1 cells (ATCC) using the calcium phosphate co-precipitation method. The plasmid pRSV-neo (ATCC) was included as a selectable marker. Clonal cell lines were selected in RPMI 1640 media containing 0.5 mg/ml of G418 (Gibco), ring cloned, and expanded into culture.

CHO-K1 cells stably expressing one of the human sst receptors are grown in RPMI 1640 containing 10% fetal calf serum and 0.4 mg/ml geneticin. Cells are collected with 0.5 mM EDTA, and centrifuged at 500 g for about 5 minutes at about 4° C. The pellet is resuspended in 50 mM Tris [hydroxymethyl]aminomethane hydrochloride, pH=7.4 at 25° C., ("Tris buffer"), and centrifuged twice at 500 g for about 5 minutes at about 4° C. The cells are lysed by sonication and centrifuged at 39,000 g for about 10 minutes at about 4° C. The pellet is resuspended in the same buffer and centrifuged at 50,000 g for about 10 minutes at about 4° C. and membranes in resulting pellet are stored at −80° C.

Competitive inhibition experiments of [$^{125}$I-Tyr$^{11}$]SRIF-14 binding are run in duplicate in polypropylene 96 well plates. Cell membranes (10 μg protein/well) are incubated with [$^{125}$I-Tyr$^1$]SRIF-14 (Dr. Tom Davis, Univ. of Arizona, Tuscon, Ariz.) (0.05 nM) for about 60 minutes at about 37° C. in 50 mM HEPES, 0.2% BSA, 2.5 mM MgCl$_2$.

Bound from free [$^{125}$I-Tyr$^{11}$]SRIF-14 is separated by immediate filtration through GF/C glass fiber filter plate (Unifilter, Packard, Meriden, Conn.) presoaked with 0.3% polyethylenimine (P.E.I.), using Filtermate 196 (Packard) cell harvester. Filters are washed with 50 mM Tris-HCl at about 0–4° C. for about 4 seconds and assayed for radioactivity using Packard Top Count.

Specific binding is obtained by subtracting nonspecific binding (determined in the presence of 0.1 μM SRIF-14) from total binding. Binding data are analyzed by computer-assisted nonlinear regression analysis (Data Analysis Toolbox, v.1.0, Molecular Design Limited, San Leandro, Calif.) and inhibition constant (Ki) values are determined.

Whether a compound of the instant invention is an SST agonist or antagonist of somatostatin is determined by the following assay.

Functional Assay: Inhibition of cAMP Intracellular Production

CHO-K1 Cells expressing human somatostatin (SRIF-14) subtype receptors are seeded in 24-well tissue culture multidishes in RPMI 1640 media with 10% fetal calf serum (FCS). The medium is changed the day before the experiment.

Cells at 10$^5$ cells/well are washed 2 times by 0.5 ml RPMI 1640 media. Fresh RPMI 1640 media with 0.2% BSA and supplemented with 0.5 mM 3-isobutyl-1-methylxanthine ("IBMX") is added, and the cells are incubated for about 5 minutes at about 37° C. Cyclic AMP production is stimulated by the addition of 1 mM forskolin ("FSK") (Sigma Chemical Co., St. Louis, Mo.) for about 15–30 minutes at about 37° C.

The agonist effect of a compound is measured by the simultaneous addition of FSK (1 μM), SRIF-14 (Bachem, Torrence, Calif.), (10$^{-12}$M to 10$^{-6}$ M) and a test compound (10$^{-10}$ M to 10$^{-5}$ M). The antagonist effect of a compound is measured by the simultaneous addition of FSK (1 μM), SRIF-14 (1 to 10 nM) and a test compound (10$^{-1}$M to 10$^{-5}$ M).

The reaction medium is removed and 200 ml 0.1 N HCl is added. cAMP is measured using radioimmunoassay method (Kit FlashPlate SMP001A, New England Nuclear, Boston).

Compounds of the instant invention can be and were assessed for its ability to bind to a neuromedin B receptor according to the following assay.

Cell Culture: Balb 3T3 cells, expressing the rat NMB receptor, were obtained from Dr. R. T. Jensen (National Institutes of Health, Bethesda, Md.), and cultured in Dulbecco's modified Eagle's medium ("DMEM") containing 10% fetal calf serum, 0.5 mg/ml of G418 (Gibco). The cells were maintained at 37° C. in a humidified atmosphere of 5% CO$_2$/95% air.

Radioligand Binding: Membranes were prepared for radioligand binding studies by homogenization of the cells in 20 ml of ice-cold 50 mM Tris-HCl with a Brinkman Polytron (Westbury, N.Y.) (setting 6, 15 sec). The homogenates were washed twice by centrifugation (39,000 g/10 minutes), and the final pellets were resuspended in 50 mM Tris-HCl containing 5.0 mM MgCl$_2$, and 0.1% BSA. For assay, aliquots (0.4 ml) were incubated with 0.05 nM [$^{125}$I-Tyr$^4$]bombesin (2200 Ci/mmol, New England Nuclear, Boston, Mass.), with and without 0.05 ml of unlabeled competing test peptides. After incubation (30 minutes, 4° C.), the bound [$^{125}$I-Tyr$^4$]bombesin was separated from the free by rapid filtration through GF/C filters (Brandel, Gaithersburg, Md.), which had been previously soaked in 0.3% polyethyleneimine. The filters were then washed three times with 5-ml aliquots of ice-cold 50 mM Tris-HCl, and the bound radioactivity trapped on the filters was counted by gamma spectrometry (Wallac LKB, Gaithersburg, Md.). Specific binding was defined as the total [$^{125}$I-Tyr$^4$] bombesin bound minus that bound in the presence of 1000 nM neuromedin B (Bachem, Torrence, Calif.).

One embodiment of the method includes the step of contacting the cells with a peptide of Formula (II):

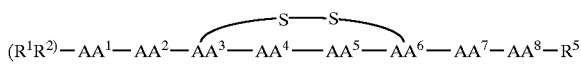

(II)

$(R^1R^{2)}-AA^1-AA^2-AA^3-AA^4-AA^5-AA^6-AA^7-AA^8-R^5$ or a pharmaceutically acceptable salt thereof,
wherein
AA$^1$ is absent or the D- or L-isomer of an amino acid selected from the group consisting of R$^{11}$, Aac, Aic, Arg, Asn, Asp, Dip, Gln, Glu, Hyp, Lys, Mac, Macab, Orn Pip, Pro, Ser, Ser(Bzl), Thr, Thr(Bzl), Pip, hArg, Bip, Bpa, Tic, Cmp, Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, I-Iqc, 3-Iqc, C4c, 5-Iqs, Htqa, 4-Mqc, Thn, α-Chpa, Cit, Nua, Pyp and an optionally substituted aromatic α-amino acid,
wherein said optionally substituted aromatic α-amino acid is optionally substituted with one or more substituents selected from the group consisting of halogen, NO$_2$, OH, CN, (C$_{1-6}$)alkyl, (C$_{2-6}$)alkenyl, (C$_{2-6}$) alkynyl, and NR$^9$R$^{10}$;
AA$^2$ is absent or the D- or L-isomer of an amino acid selected from the group consisting of R$^{11}$, Aic, Arg, Hca, His, Hyp, Pal, F$_5$-Phe, Phe, Pro, Trp, X$^0$-Phe, Pip, hArg, Bip, Bpa, Tic, Cmp Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, I-Iqc, 3Iqc, C4c, 5-Iqs, Htqa, 4-Mqc, Thn, α-Chpa, Cit, Nua, and Pyp;AA$^3$ is the D- or L-isomer of an amino acid selected from the group consisting of Cys, hCys, Pen, Tpa and Tmpa;
AA$^4$ is a D- or L-isomer of an amino acid selected from the group consisting of Trp, N-Met-Trp, β-Met-Trp, His, hHis, hArg, Bip, Tic, Htic, Dip, Sala, Aala, Thza, Thia, Bal, Fala, Pala, and an optionally substituted aromatic α-amino acid,
wherein said optionally substituted aromatic α-amino acid is optionally substituted with one or more substituents each independently selected from the group consisting of halogen, NO$_2$, OH, (C$_{1-4}$)alkyl, (C$_{2-4}$) alkenyl, (C$_{2-4}$)alkynyl, Bzl, O-Bzl, and NR$^9$R$^{10}$;
AA$^6$ is a D- or L-isomer of an amino acid selected from the group consisting of 4-Pip-Gly, 4-Pip-Ala, cis-4-Acha, trans-4-Acha, trans-4-Amcha, hLys, Lys, Orn, hArg, Bip, Tic Htic, Dip, Sala, Aala, Thza, Thia, Bal, Fala, and Pala,
wherein the side-chain amino group of said amino acid is optionally mono- or di-substituted with $R^3$ and $R^4$;

$AA^6$ is a D- or L-isomer of an amino acid selected from the group consisting of Cys, hCys, Pen, Tpa, and Tmpa;

$AA^7$ is absent or a D- or L-isomer of an amino acid selected from the group consisting of $R^{11}$, Aic, A3c, A4c, A5c, A6c, Abu, Aib, β-Ala, Arg, Bpa, Cha, Deg, Gaba, His, Ile, Leu, Nal, Nle, Pal, Phe, $F_5$-Phe, Pro, Sar, Ser, Ser(Bzl), Thr, Thr(Bzl), Trp, N-Me-Trp, Val, N-Me-Val, hArg, Bip, Tic, Htic, Dip, Sala, Aala, Thza, Thia, Bal, Fala, Pala, and $X^0$-Phe;

$AA^8$ is absent or the D- or L-isomer of an amino acid selected from the group consisting of $R^{11}$, an optionally substituted aromatic α-amino acid, Maa, Maaab, Ser, Ser(Bzl), Thr, Thr(Bzl), Tyr, Phe(4-O-Bzl), $F_5$-Phe, and $X^5$-Phe;

$R^{13}$ is a moiety according to the formula

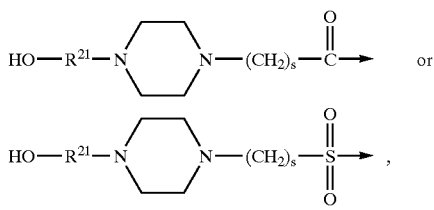

wherein $R^{21}$ is $(C_{1-4})$alkyl and s is 1, 2, 3, or 4; and $X^0$ is halogen, $NO_2$, $CH_3$, OH, Bzl, O-Bzl or CN;

provided that at least one of $AA^7$ or $AA^8$ is present

Another embodiment of the method includes the step of contacting the cells with a peptide of Formula (III):

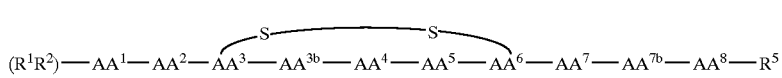

(III)

or a pharmaceutically acceptable salt thereof, wherein
$AA^1$ is absent or the D- or L-isomer of an amino acid selected from the group consisting of $R^{11}$, Aac, Aic, Arg, Asn, Asp, Gin, Glu, Hca, His, Hyp, Lys, Mac, Macab, Orn, Pro, Ser, Ser(Bzl), Thr, Thr(Bzl), Pip, hArg, Bip, Bpa, Tic, Cmp, Inc, Inp, Nip, Ppc, Htic, Thi, Tra, Cmpi, Tpr Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, 1-Iqc, 3-Iqc, C4c, 5-Iqs, Htqa, 4-Mqc, Thn, α-Chpa, Cit, Nua, Pyp and an optionally substituted aromatic α-amino acid,
wherein said optionally substituted aromatic α-amino acid is optionally substituted with one or more substituents selected from the group consisting of halogen, $NO_2$, OH, CN, $(C_{1-6})$alkyl, $(C_{2-4})$alkenyl, $(C_{2-6})$alkynyl, and $NR^9R^{10}$;

$AA^3$ is a D- or L-isomer of an amino acid selected from the group consisting of Cys, hCys, Pen, Tpa, and Tmpa;

$AA^{3b}$ is the D- or L-isomer of an amino acid selected from the group consisting of $R^{11}$, Arg, Bpa, $F_5$-Phe, His, Nal, Pal, 4-Pal, Phe, Trp, erg, Bip, Tic, Htic, Dip, Sala, Aala, Thza, Thia, Bal, Fala, Pala, and $X^5$-Phe; AA is a D- or L-isomer of an amino acid selected from the group consisting of Trp, N-Met-Trp, β-Met-Trp, His, hHis, hArg, Bip, Tic, Htic, Dip, Sala, Aala, Thza, Thia, Bal, Fala, Pala, and an optionally substituted aromatic α-amino add;

wherein said optionally substituted aromatic α-amino acid is optionally substituted with one or more substituents each independently selected from the group consisting of halogen, $NO_2$, OH, CN, $(C_{1-4})$alkyl, $(C_{2-4})$alkenyl, $(C_{2-4})$alkynyl, Bzl, O-Bzl, and $NR^9R^{10}$;

$AA^5$ is a D- or L-isomer of an amino acid selected from the group consisting of 4-Pip-Gly, 4-Pip-Ala, cis-4-Acha, trans-4-Acha, trans-4-Amcha, hLys, Lys and Orn, and, hArg, Bip, Tic, Htic, Dip, Sala, Aala, Thza, Thia, Bal, Fala, Pala,
wherein the side-chain amino group of said amino acid is optionally mono- or disubstituted with $R^3$ and $R^4$;

$AA^6$ is a D- or L-isomer of an amino acid selected from the group consisting of Cys, hCys, Pen, Tpa, and Tmpa;

$AA^7$ is absent or a D- or L-isomer of an amino acid selected from the group consisting of $R^{11}$, Aic, A3c, A4c, A5c, A6c, Abu, Aib, β-Ala, Arg, Bpa, Cha, Deg, Gaba, His, Ile, Leu, Nal, Nle, Pal, Phe, $F_5$-Phe, Pro, Sar, Ser, Ser(Bzl), Thr, Thr(Bzl), Trp, N-Me-Trp, Val, N-Me-Val, hArg, Bip, Tic, Htic, Dip, Sala, Aala, Thza, Thia, Bal, Fala, Pala, and $X^0$-Phe;

$X^0$ is halogen, $NO_2$, $CH_3$, OH, CN, Bzl or O-Bzl;

$R^1$ and $R^2$ each is, independently, H, E-, $E(O)_2S$—, $E(O)C$—, EOOC—, $R^{13}$, or absent;

$R^5$ is —$OR^6$ or —$NR^7R^8$;

$R^{13}$ is a moiety of the formula

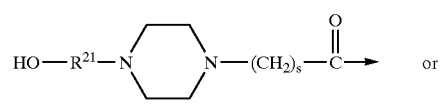

-continued wherein $R^{21}$ is $(C_{1-4})$alkyl and s is 1, 2, 3, or 4; provided that:

at least one of $AA^1$ or $AA^2$ is present;

when $AA^1$ is a D- or L-isomer of Pro, Hyp, Arg, Pip, hArg, Bip, Bpa, Tic, Cmp Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, 1-Iqc, 3-Iqc, C4c, 5-Iqs, Htqa, 4 Mqc, Thn, α-Chpa, Cit, Nua, Pyp or His, $AA^2$ cannot be a D- or L-isomer of Pro, Hyp, Arg, Pip, hArg, Bip, Bpa, Tic, Cmp, Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, 1-Iqc, 3-Iqc, C4c, 5-Iqs, Htqa, 4-Mqc, Thn, α-Chpa, Cit, Nua, Pyp or His;

when $AA^7$ is a D- or L-isomer of Thr or of Ser, $AA^8$ cannot be a D- or L-isomer of Thr or of Ser;

at least one of AA¹, AA², AA³ᵇ, AA⁷, AA⁷ᵇ, or AA⁸ is the D- or L-isomer of R¹¹; and when one of X² or X³ is =O or =S, the other is absent;

or a pharmaceutically acceptable salt thereof.

Yet another embodiment of the method includes the step of contacting the cells with a peptide of Formula (IV):

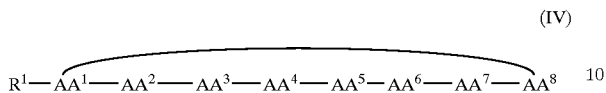

(IV)

wherein

AA¹ is absent, the D- or L-isomer of an amino acid selected from the group consisting of R¹¹, Aic, Hyp, Pro, Ser, Ser(Bzl), Thr, Thr(Bzl), and an optionally substituted aromatic α-amino acid;
wherein said optionally substituted aromatic α-amino acid is optionally substituted with one or more substituents each independently selected from the group consisting of halogen, NO₂, OH, (C₁₋₆)alkyl, (C₂₋₆) alkenyl, (C₂₋₆)alkynyl, (C₁₋₆)alkoxy, Bzl, O-Bzl, and NR⁹R¹⁰;

AA² is absent or the D- or L-isomer of an amino acid selected from the group consisting of R¹¹, Arg, F₅-Phe, His, Pal, Phe, Trp, and X⁰-Phe;

AA² is the D- or L-isomer of an optionally substituted aromatic α-amino acid, wherein said optionally substituted aromatic α-amino add is optionally substituted with one or more substituents selected from the group consisting of halogen, NO₂, OH, (C₁₋₄)alkyl, (C₂₋₄)alkenyl, (C₂₋₄)alkynyl, Bzl, O-Bzl, and NR⁹R¹⁰;

AA⁴ is a D- or L-isomer of an optionally substituted amino acid selected from the group consisting of Lys, Orn, hLys, cis-4-Acha, trans-4-Acha, trans-4-Amcha, 4-Pip-Gly, and 4-Pip-Ala,
wherein the side chain amino group of said optionally substituted amino acid is optionally substituted with R³ and R⁴;

AA⁵ is absent or a D- or L-isomer of R¹¹, A3c, A4c, A5c, A6c, Abu, Aib, Aic, β-Ala, Bpa, Cha, Deg, F₅-Phe, Gaba, Ile, Leu, Nal, Nle, Pal, Phe, Pro, Sar, Ser, Ser(Bzl), Thr, Thr(Bzl), Trp, N-Me-Trp, Val, N-Me-Val, or X⁰-Phe;

AA⁶ is absent, the D- or L-isomer of R¹¹, an aromatic α-amino acid, F₅-Phe, Phe, Thr, Thr(Bzl), Ser, Ser(Bzl), or X⁰-Phe;

AA⁷ is absent, the D- or L-isomer of R¹¹ or the D- or L-isomer of an aromatic α-amino acid;

AA⁸ is a D- or L- isomer of R¹³;

R¹ is H, E-, E(O)₂S—, E(O)C—, EOOC—, or R¹³;

R¹³ is a moiety of the formula

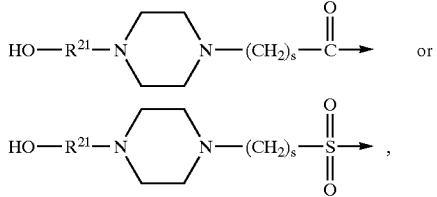

or wherein R²¹ is (C₁₋₄)alkyl and s is 1, 2, 3, or 4;

X⁰ in the definition of AA² and AA⁵ is halogen, NO₂, OH, (C₁₋₆)alkyl, (C₁₋₆)alkoxy, mono- or di-(C₁₋₆)alkylamino, Bzl or O-Bzl;

X⁰ in the definition of AA⁶ is halogen, NO₂, OH, (C₁₋₆) alkyl, (C₁₋₆)alkoxy, mono- or di-(C₁₋₆)alkylamino, Bzl, O-Bzl, or NR⁹R¹⁰; provided that:

at least one of AA¹ or M² is present;

when AA¹ is absent, AA² and AA⁸ together form a bond; and at least two of AA⁵, AA⁶, and AA⁷ are present, or a pharmaceutically acceptable salt thereof.

Abbreviations (A(z))aeg (A)aeg where the amino group of the adenine moiety is protected with carbobenzyloxy, i.e.,

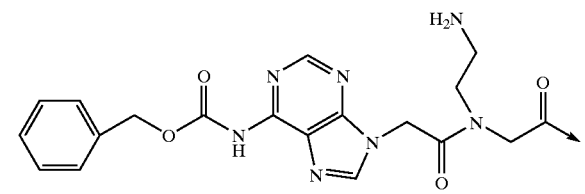

(A)aeg N-(2-aminoethyl)-N-(2-adeninyl-1-oxo-ethyl)-glycine (C(z))aeg (C)aeg where the amino group of the cytosine moiety is protected with carbobenzyloxy,

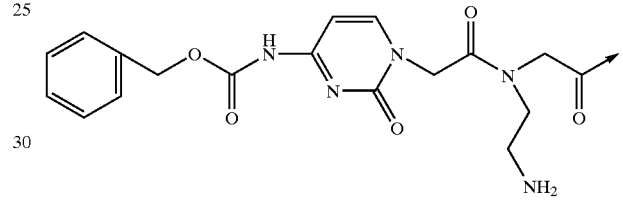

ie., (C)aeg N-(2-aminoethyl)-N-(2-cytosinyl-1-oxo-ethyl)-glycine (G(z))aeg (G)aeg where the amino group of the guanine moiety is protected with carbobenzyloxy, i.e.,

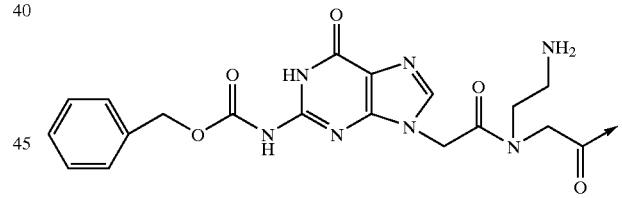

(G)aeg N-(2-aminoethyl)-N-(2-guaninyl-1-oxo-ethyl)-glycine (T)aeg N-(2-aminoethyl)-N-(2-thyminyl-oxo-ethyl)-glycine A3c 1-Amino-1-cyclopropane-1-carboxylic acid A4c 1-Amino-1-cyclobutane-1-carboxylic acid A5c 1-Amino-1-cyclopentane-1-carboxylic acid A6c 1-Amino-1-cyclohexane-1-carboxylic acid Aaa 2-Aminoanthraquinone Aac an aminoalkyl carboxylic acid of the formula H₂N—(CH₂)ₙ—COOH, wherein n is 2–6

Aala Anthrylalanine

Aba N-(4-aminobenzoyl)-β-alanine

Abp 4-amino-1-benzylpiperidine

Abu 2-Aminobutyric Acid

Ac acetyl, i.e., CH3—C(O)—;

Ach trans-1,4-Diaminocyclohexane

4-Acha 3-(4-aminocyclohexyl)alanine

Ads 1-Amino-deoxy-D-sorbitol aeg Aminoethylglycine

Agly Allylglycine
Ahep 1-Amino-4-(2-hydroxyethyl) Piperazine
Aib 2-Aminoisobutyric Acid
Aic 2-aminoindan-2-carboxylic acid
5Aiq 5-Amino Isoquinoline
Alla Allantoic add
4-Amcha 3-((4-aminomethyl)cyclohexyl)alanine
Amp 1-Amino-4-methylpiperazine
Apa 2,3-Diaminopropionic acid
Api 1-(3-Aminopropyl)imidazole
Bal 3-Benzothienylalanine
Bip 4,4'-Biphenylalanine
BOC Tertiarybutyloxycarbonyl
Bpa 3-(4-biphenyl)alanine
Bzl the benzyl radical
Bzop 4-Benzoylphenylalanine
C4c Cinnoline-4-Carboxylic add
Car Carnosine
Cbz carbobenzyloxy radical
Cha 3-Cyclohexylalanine
α-Chpa Alpha-cyclohexylphenylacetic acid
Cit citrinin
Cmp 4-Carboxymethylpiperidine
Cmpi 4-Carboxymethylpiperazine
Cpa 2-, 3-, or 4-chloro phenylalanine, unless otherwise indicated
Dap 2,3-Diaminopropionic acid
Dapy 2,6-Diaminopyridine
DCM dichloromethane
Deg Diethylglycine
D-Ga D-Glucosamine
Dip 3,3-Diphenylalanine
DiPa 3,5-Diiodo-4-Pyridone-1-acetic acid
DIPEA diisopropylethylamine
DMF dimethylformamide
Edp 4,4'-Ethylenedipiperidine
Edt 4,4'-Ethylenedi-m-toluidine
$F_5$-Phe 3-(Pentafluorophenyl)-alanine
Fala 2-Furylalanine
FMOC 9-Fluorenylmethoxycarbonyl
Fpp 1-(4-Fluorophenyl)piperazine
Gaba 4-Aminobutyric Acid
Gba 4-Guanidinobenzoic acid
HATU O-(7-azabenzotriazolyl)-1,1,3,3-tetramethyluronuim hexafluorophosphate
HBTU O-(benzotriazol-1-yl)-1,1,3,3-tetramethyluronuim hexafluorophosphate
Hca Hydrocinnamic acid (3-phenylpropionic acid)
hCys homocysteine
Hep 1-(2-Hydroxyethyl)piperazine
hLys homolysine
HOAT 1-hydroxy-7-azabenzotriazole
Htic 1,2,3,4-tetrahydroisoquinoline-7-hydroxy-3-carboxylic acid
Htqa 4-Hydroxy-7-Trifluoromethyl-3-quinoline carboxylic acid
Hyd Hydralazine
Hyp 4-Hydroxyproline
Iaa N-(3-Indolylacetyl)-L-Alanine
Iia 2-Imino-1-imidazolidine acetic acid
Ina N-(3-Indolylacetyl)L-Phenylalanine
Inc Indoline-2-Carboxylic Acid
Inic Isonicotinic acid
Inip Isonipecotic acid
Ipa 3-Indole Propionic Acid
1-Iqc 1-Isoquinolinecarboxylic acid
3-Iqc 3 Isoquinolinecarboxylic acid
5-Iqs 5-Isoquinoline sulfonic Acid

Lys with its ε amino group substituted with $R^3$ and $R^4$
Lys(diEt) Lys with its ε amino group disubstituted by two ethyl groups
Lys(iPr) Lys with its ε amino group monosubstituted by an isopropyl group
Maa a mercaptoalkyl amine of the formula HS—$(CH_2)_n$—$NH_2$, wherein n is 2–6;
Maaab a o-, m-, or p-(mercaptoalkyl)(aminoalkyl)benzene of the formula

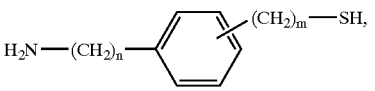

wherein m and n each is, independently, 0, 1, or 2.
Mac a mercaptoalkyl carboxylic acid of the formula HS—$(CH_2)_n$—COOH, wherein n is 2–6;
Macab a o-, m-, or p-(mercaptoalkyl)(carboxyalkyl)benzene of the formula

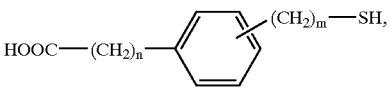

wherein m and n each is, independently, 0, 1, or 2.
MBHA 4-methylbenzhydrylamine
Me-Trp Trp with its indolyl nitrogen substituted with methyl
Mim Mimosine
Mnf 5-(4-methyl-2-nitrophenyl)-2-furoic acid
Mpip 1-Methylpiperazine
4-Mqc 4-methoxy-2-quinolinecarboxylic acid
Nal 3-(2-naphthyl)-alanine, unless otherwise indicated
Nip Nipecotic acid
Nle norleucine
Nua Nicotinuric acid
O-Bzl the benzyloxy radical
Orn ornithine

Orn with its amino group substituted with $R^3$ and $R^4$
Pal 3-(3-Pyridyl)-alanine, unless otherwise indicated
2-Pala 2-Pyridylalanine
3-Pala 3-Pyridylalanine
4-Pala 4-Pyridylalanine
Pap 4'-piperazinoacetophenone
Pen penicillamine
Pgly Propargylglycine
Phg phenylglycine
Pip pipecolinic acid
4-Pip-Ala 3-(4-piperidyl)alanine
4-Pip-Gly (4-piperidyl)glycine
Pnf para-Nitro-phenylalanine (i.e., 4-Nitro-phenylalanine)
Ppc 4-Phenylpiperidine-4-carboxylic Acid
Pyp 3-pyridine propionic acid Sala Styrylalanine
Sar sarcosine (i.e., N-methylglycine)
Thi Thiaproline
2-Thia 2-Thienylalanine
3-Thia 3-Thienylalanine
Thn 1, 2, 3, 4-Tetrahydro-2-naphthoic acid
Thnc 1,2,3,4-Tetrahydronorbarman-3-carboxylic acid
Thza 4-Thiazolylalanine
Tic 1,2,3,4-tetrahydro-3-isoquinolinecarboxylic acid
Tmpa 3-(p-thiomethylphenyl)-alanine
Tpa 3-(p-thiophenyl)-alanine
Tpr Thioproline
Tra Tranexamic acid
TrPa Tryptamine
X-Phe phenylalanine with p-, o- or m-substituents X on its benzene ring, e.g., 3-(4-chlorophenyl)-alanine
z carbobenzyloxy Administration of a pharmaceutically acceptable salt of a compound covered by formula (I) into a patient whose disorder arises from biochemical activity induced by NMB or somatostatin is also within the present invention. In other words, the peptides can be provided in the form of pharmaceutically acceptable salts, e.g., acid addition salts, or metal complexes, e.g., with zinc, iron or the like. Illustrative examples of acid addition salts are those with organic acids such as acetic, lactic, pamoic, maleic, citric, malic, ascorbic, succinic, benzoic, palmitic, suberic, salicylic, tartric, methanesulfonic or toluenesulfonic acid, those with polymeric acids such as tannic acid or carboxymethyl cellulose, and those with inorganic acids such as hydrochloric acid, hydrobromic acid, sulfuric acid or phosphoric acid.

Other features and advantages of the present invention will be apparent from the following description of the preferred embodiments, and also from the claims. It is believed that one skilled in the art can, based on the description herein, utilize the present invention to its fullest extent. The following specific embodiments are therefore to be construed as merely illustrative and not limitative of the remainder of the disclosure in any way whatsoever. All of the documents cited herein are hereby incorporated by reference

DESCRIPTION OF THE PREFERRED EMBODIMENTS

In a preferred embodiment the invention features a compound according to Formula II, wherein
$AA^1$ is absent, Ac-D-Phe, or the D- or L- isomer of $R^{11}$, Pip, Pro, or Ser, or of an aromatic α-amino acid selected from the group consisting of Cpa, Dip, Nal, Pal, and Phe;
$AA^2$ is Aic, Pal, Phe, $F_5$-Phe, 4-$NO_2$-Phe, Trp, Tyr, Phe(4-O-Bzl), or absent;
$AA^3$ is the D- or L- isomer of an amino acid selected from the group consisting of Pen, Cys, hCys and Tmpa;
$AA^4$ is the D- or L-isomer of Trp or of His;
$AA^5$ is Lys, hLys, N-Me-Lys, Orn, cis-4-Acha or 4-Pip-Ala;
$AA^6$ is the D- or L-isomer of an amino acid selected from the group consisting of Cys, hCys, Pen and Tmpa;
$AA^7$ is A3c, A4c, A5c, A6c, Abu, Aic, β-Ala, Gaba, Nle, $F_5$-Phe, Phe, Pro, Sar, Ser, Thr, Thr(Bzl), Tyr, Val or absent; and
$AA^8$ is $R^{11}$, Nal, Thr, Thr(Bzl), Tyr, Phe(4-O-Bzl), or absent;
or a pharmaceutically acceptable salt thereof.

In a more preferred embodiment the invention features a compound according to the immediately foregoing, wherein
$AA^1$ is absent or the D- or L- isomer of $R^{11}$, Pip or Pro, or of an aromatic α-amino acid selected from the group consisting of Cpa, Dip, Nal, Pal, Phe, and Ac-Phe;
$AA^2$ is Tyr, Pal, Phe, 4-$NO_2$-Phe, Trp, or absent,
$AA^3$ is a D- or L-isomer of Cys or Pen;
$AA^4$ is D-Trp;
$AA^5$ is Lys, Orn, or cis-4-Acha;
$AA^6$ is a D- or L-isomer of Cys or Pen;
$AA^7$ is A3c, A4c, A5c, A6c, Abu, Aic, β-Ala, Gaba, Nle, Phe, Pro, Sar, Thr, Thr(Bzl), Tyr, Val, or absent; and
$AA^8$ is $R^{11}$, Thr, Tyr, Nal, or absent;
or a pharmaceutically acceptable salt thereof.

In another preferred embodiment the invention features a compound according to Formula III, wherein
$AA^1$ is $R^{11}$, Aic, Hca, Pro, Ser, Ser(Bzl), Trp, Tyr, or a D- or L-isomer of an aromatic α-amino acid selected from the group consisting of Cpa, Nal, Ac-Nal, Phe, Ac-Phe, 4-$NO_2$-Phe, and Ac-4-$NO_2$-Phe;
$AA^2$ is Pal, Phe, $F_5$-Phe, Tyr, or absent;
$AA^3$ is a D- or L-isomer of Cys, hCys, Pen or Tmpa;
$AA^{3b}$ is Pal, 4-Pal, His, Trp, Tyr, Phe(4-O-Bzl), Phe, or $R^{11}$;
$AA^4$ is a D- or L-isomer of Trp or His;
$AA^5$ is Lys, N-Me-Lys, Orn, hLys, cis-4-Acha, or 4-Pip-Ala;
$AA^6$ is a D- or L-isomer of Cys, hCys, Pen or Tmpa;
$AA^7$ is $R^{11}$, A4c, A5c, Abu, β-Ala, Gaba, Phe, $F_5$-Phe, Ser(Bzl), Thr, Thr(Bzl), Phe(4-O-Bzl), or absent;
$AA^{7b}$ is $R^{11}$, Nal, $F_5$-Phe, $X^0$-Phe or absent, wherein $X^0$ is halogen, $NO_2$, $CH_3$, OH, Bzl or O-Bzl; and
$AA^8$ is $R^{11}$, Nal, Tyr, Phe(4-O-Bzl), or absent;
or a pharmaceutically acceptable salt thereof.

In a more preferred embodiment the invention features a compound according to the immediately foregoing, wherein
$AA^1$ is $R^{11}$, Aic, Hca, Pro, Ser(Bzl), or a D- or L-isomer of an aromatic α-amino acid selected from the group consisting of Cpa, Nal, Ac-Nal, Phe, Ac-Phe, 4-$NO_2$-Phe, and Ac-4-$NO_2$-Phe;
$AA^2$ is Pal, Tyr, or absent;
$AA^3$ is a D- or L-isomer of Cys or Pen;
$AA^{3b}$ is $R^{11}$, Pal, 4-Pal, Trp, Tyr, Phe(4-O-Bzl), or Phe, wherein $R^{11}$ is (T)aeg;
$AA^4$ is D-Trp;
$AA^5$ is Lys, N-Me-Lys, Orn, or cis-4-Acha;
$AA^6$ is a D- or L-isomer of Cys or Pen;
$AA^7$ is $R^{11}$, A5c, Abu, Ser(Bzl), Thr, Thr(Bzl), Phe(4-O-Bzl), Gaba, or absent;
$AA^{7b}$ is Nal, $X^0$-Phe or absent; and
$AA^8$ is Tyr or absent;
or a pharmaceutically acceptable salt thereof.

In yet another preferred embodiment the invention features a compound according to Formula IV, wherein
$AA^1$ is Aic, Hyp, Cpa, D-Cpa, Nal, Pal, Phe, Pro, $R^{11}$, Tyr or absent;
$AA^2$ is Phe, Trp, $F_5$-Phe, His, Tyr, Phe(4-O-Bzl), or $R^{11}$; $AA$ is a D-isomer of Trp, His, or Pal;
$AA^4$ is Lys, N-Me-Lys, Orn, hLys, cis-4-Acha, or 4-Pip-Ala;
$AA^5$ is Pal, Phe(4-O-Bzl), Thr(Bzl), Thr, Sar, Gaba, β-Ala, A4c, A5c, A6c, Abu, Aic or absent;
$AA^6$ is Thr, Tyr, Ser, $F_5$-Phe, Cpa, Nal, or D- or L-Phe;
$AA^7$ is Nal, Pal, or absent; and
$AA^8$ is $R^{11}$;
or a pharmaceutically acceptable salt thereof.

In yet another more preferred embodiment the invention features a compound according to the immediately foregoing, wherein
$AA^1$ is Cpa, Nal, Pal, Phe, Tyr or absent;
$AA^2$ is Phe, Tyr, Trp, or $R^{11}$;
$AA^3$ is D-Trp;
$AA^4$ is Lys, N-Me-Lys, or cis-4-Acha;
$AA^5$ is Pal, Phe(4-O-Bzl), Aic, Gaba, A5c or absent;
$AA^6$ is Thr, Nal, or D- or L-Phe;

AA⁷ is absent; and
AA⁸ is R¹¹;
or a pharmaceutically acceptable salt thereof.

In still yet another preferred embodiment the invention features a compound according to Formula II, wherein R¹ and R⁵ are absent and the N-terminal amino acid and the C-terminal amino acid together form an amide bond; or a pharmaceutically acceptable salt thereof.

In still yet another preferred embodiment the invention features a compound according to Formula III), wherein R¹ and R⁵ are absent and the N-terminal amino acid and the C-terminal amino acid together form an amide bond; or a pharmaceutically acceptable salt thereof.

In a most preferred embodiment the invention features a compound according to Formula II, wherein said compound is of the formula:

Ac-D-Phe-Tyr-cyclo(D-Cys-D-Trp-Lys-Cys)-Abu-Thr-NH₂;
Nal-Tyr-cyclo(Cys-D-Trp-Lys-D-Cys)-Val-Nal-NH₂;
Nal-Tyr-cyclo(Cys-D-Trp-Lys-D-Cys)-Abu-Nal-NH₂;
D-Dip-Tyr-cyclo(Cys-D-Trp-Lys-D-Cys)-Abu-Nal-NH₂;
Dip-Tyr-cyclo(D-Cys-D-Trp-Lys-D-Cys)-Abu-Nal-NH₂:
Nal-Tyr-cyclo(D-Cys-D-Trp-Lys-D-Cys)-Abu-Nal-NH₂;
Dip-Tyr-cyclo(D-Cys-D-Trp-Lys-D-Cys)-Val-Nal-NH₂;
Nal-Tyr-cyclo(D-Cys-D-Trp-Lys-D-Cys)-Val-Nal-NH₂;
cyclo(D-Phe-Tyr-cyclo(D-Cys-D-Trp-Lys-Cys)-Abu-Thr);
Cpa-Pal-cyclo(D-Cys-D-Trp-Lys-D-Cys)-A3c-Nal-NH₂;
Cpa-Pal-cyclo(D-Cys-D-Trp-Lys-D-Cys)-A5c-Nal-NH₂;
Cpa-Pal-cyclo(D-Cys-D-Trp-Lys-D-Cys)-A6c-Nal-NH₂;
(G(z))aeg-cyclo(D-Cys-D-Trp-Lys-D-Cys)-A5c-Nal-NH₂;
Pal-cyclo(D-Cys-D-Trp-Lys-D-Cys)-A5c-Nal-NH₂;
Cpa-Pal-cyclo(D-Cys-D-Trp-Lys-D-Cys)-β-Ala-Nal-NH₂;
Cpa-Pal-cyclo(D-Cys-D-Trp-Lys-D-Cys)-Sar-Nal-NH₂;
Cpa-Pal-cyclo(D-Cys-D-Trp-Lys-D-Cys)-Gaba-Nal-NH₂; or
Cpa-Pal-cyclo(D-Cys-D-Trp-Lys-D-Cys)-Pro-Nal-NH₂;
or a pharmaceutically acceptable salt thereof.

In another most preferred embodiment the invention features a compound according to Formula II, wherein said compound is of the formula:

Phe-cyclo(Cys-D-Trp-Lys-Cys)-Thr-NH₂;
Phe-Tyr-cyclo(D-Cys-D-Trp-Lys-Cys)-Abu-Thr-NH₂;
Ac-D-Phe-Tyr-cyclo(D-Cys-D-Trp-Lys-Cys)-Abu-Thr-NH₂;
Nal-Tyr-cyclo(Cys-D-Trp-Lys-D-Cys)-Val-Nal-N H₂;
Nal-Tyr-cyclo(Cys-D-Trp-Lys-D-Cys)-Abu-Nal-NH₂;
Dip-Tyr-cyclo(D-Cys-D-Trp-Lys-D-Cys)-Abu-Nal-NH₂;
Nal-Tyr-cyclo(D-Cys-D-Trp-Lys-D-Cys)-Abu-Nal-NH₂;
Dip-Tyr-cyclo(D-Cys-D-Trp-Lys-D-Cys)-Val-Nal-NH₂;
Nal-Tyr-cyclo(D-Cys-D-Trp-Lys-D-Cys)-Val-Nal-N H₂;
Cpa-Pal-cyclo(D-Cys-D-Trp-Lys-D-Cys)-A3c-Nal-NH₂;
Cpa-Pal-cyclo(D-Cys-D-Trp-Lys-D-Cys)-A5c-Nal-NH₂;
Cpa-Pal-cyclo(D-Cys-D-Trp-Lys-D-Cys)-A6c-Nal-NH₂;
(G (z))aeg-cyclo(D-Cys-D-Trp-Lys-D-Cys)-A5c-Nal-NH₂;
D-Cpa-cyclo(Cys-D-Trp-Lys-D-Cys)-A5c-Nal-NH₂;
Pal-cyclo(D-Cys-D-Trp-Lys-D-Cys)-A5c-Nal-NH₂;
Cpa-cyclo(D-Cys-D-Trp-Lys-D-Cys)-A5c-Nal-NH₂;
Cpa-Pal-cyclo(D-Cys-D-Trp-Lys-D-Cys)-β-Ala-Nal-NH₂;
Cpa-Pal-cyclo(D-Cys-D-Trp-Lys-D-Cys)-Sar-Nal-NH₂;
Cpa-Pal-cyclo(D-Cys-D-Trp-Lys-D-Cys)-Aic-Nal-NH₂;
Cpa-Pal-cyclo(D-Cys-D-Trp-Lys-D-Cys)-Gaba-Nal-NH₂;
Cpa-Pal-cyclo(D-Cys-D-Trp-Lys-D-Cys)-Pro-Nal-NH₂;
(T)aeg-cyclo(D-Cys-D-Trp-Lys-D-Cys)-(A)aeg-NH₂;
Cpa-Pal-cyclo(D-Cys-D-Trp-Lys-D-Cys)-A4c-Nal-NH₂;
Cpa-Pal-cyclo(D-Cys-D-Trp-Lys-D-Cys)-Nal-NH₂;
Pal-cyclo(D-Cys-D-Trp-Lys-D-Cys)-Nal-NH₂;
Pro-Phe-cyclo(Cys-D-Trp-Lys-D-Cys)-Val-NH₂;
Pro-Phe-cyclo(D-Cys-D-Trp-Lys-Cys)-Val-NH₂;
Pip-4-NO₂-Phe-cyclo(D-Cys-D-Trp-Lys-D-Cys)-Nle-NH₂;
(G)aeg-Pal-cyclo(D-Cys-D-Trp-Lys-D-Cys)-Thr(Bzl)(G) aeg-NH₂;
(C)aeg-Pal-cyclo(D-Cys-D-Trp-Lys-D-Cys)Thr(Bzl)-(G) aeg-NH₂;
Pro-Phe-c(D-Cys-D-Trp-Lys-Cys)-Nle-Phe-NH₂;
Pro-Phe-c(D-Cys-D-Trp-Lys-D-Cys)-Thr-Nle-NH₂;
Pro-Phe-c(D-Cys-D-Trp-Lys-D-Cys)-Thr-Phe-NH₂;
Cpa-Phe-c(D-Cys-D-Trp-Lys-D-Cys)-Gaba-NH₂;
Cpa-Phe-c(D-Cys-D-Trp-Lys-D-Cys)-Gaba-Tyr-NH₂;
Pip-Phe-c(D-Cys-D-Trp-Lys-D-Cys)-N H₂;
Pip-Phe-c(Cys-D-Trp-Lys-Cys)Gaba-NH₂; or
Pro-Phe-c(D-Cys-D-Trp-Lys-D-Cys)Thr-NH₂;
or a pharmaceutically acceptable salt thereof.

In yet another most preferred embodiment the invention features a compound according to Formula III, wherein said compound is of the formula:

Nal-cyclo(D-Cys-Tyr-D-Trp-Lys-Cys)-Nal-NH₂;
D-Nal-cyclo(D-Cys-Tyr-D-Trp-Lys-Cys)-Nal-NH₂;
D-Phe-cyclo(Cys-Tyr-Trp-Lys-Cys)-Thr-NH₂;
D-4-NO₂-Phe-cyclo(D-Cys-Tyr-D-Trp-Lys-Cys)-Nal-NH₂;
Ac-D4-NO₂-Phe-cyclo(D-Cys-Tyr->Trp-Lys-Cys)-Nal-NH₂;
D-4-NO₂-Phe-Pal-cyclo(D-Cys-Phe(4-O-Bzl)-D-Trp-Lys-Cys)-Tyr-NH₂;
Cpa-cyclo(D-Cys-Pal-D-Trp-Lys-Cys)-Thr(Bzl)-Tyr-N H₂;
D-4-NO₂-Phe-cyclo(D-Cys-Pal-D-Trp-Lys-Cys)-Thr-Tyr-NH₂;
D-4-NO₂-Phe-cyclo(D-Cys-Pal-D-Trp-Lys-Cys)-Thr(Bzl)-NH₂;
D4-NO₂-Phe-cyclo(D-Cys-Pal-Trp-Lys-D-Cys)-Thr(Bzl)-Tyr-NH₂;
D-4-NO₂-Phe-cyclo(D-Cys-Tyr-D-Trp-Lys-Cys)-Thr(Bzl)-Tyr-NH₂;
D-4-NO₂-Phe-cyclo(D-Cys-Pal-D-Trp-Lys-Cys)-Thr(Bzl)-Tyr-NH₂;
D-Nal-cyclo(D-Cys-Pal-D-Trp-Lys-Cys)-Thr(Bzl)-Tyr-NH₂:
Pro-cyclo(D-Cys-Pal-D-Trp-Lys-Cys)-Thr(Bzl)-Tyr-NH₂;
Cpa-cyclo(D-Cys-Pal-D-Trp-Lys-Cys)-Thr(Bzl)-Nal-NH₂;
Ser(Bzl)-cyclo(D-Cys-Pal-D-Trp-Lys-Cys)-Thr-Tyr-NH₂;
(T)aeg-cyclo(D-Cys-Pal-D-Trp-Lys-D-Cys)-Thr(Bzl)-Tyr-N H₂;
(T)aeg-cyclo(D-Cys-Pal-D-Trp-Lys-Cys)-Thr(Bzl)-Tyr-NH₂:
(T)aeg-cyclo(D-Cys-Pal-D-Trp-Lys-Cys)-Thr(Bzl)-Tyr-NH₂;
(T)aeg-cyclo(D-Cys-Pal-D-Trp-Lys-Cys)-Thr(Bzl)-Tyr-NH₂;
(T)aeg-cyclo(D-Cys-Tyr-D-Trp-Lys-Cys)-Thr(Bzl)-Tyr-NH₂;
(T)aeg-cyclo(D-Cys-Phe-D-Trp-Lys-Cys)-Thr(Bzl)-Tyr-NH₂;
(T)aeg-cyclo(D-Cys-(T)aeg-D-Trp-Lys-Cys)-Thr(Bzl)-Tyr-NH₂;
(T)aeg-cyclo(D-Cys-Pal-D-Trp-Lys-Cys)-Ser(Bzl)-Tyr-NH₂;
(T)aeg-cyclo(D-Cys-Pal-D-Trp-Lys-Cys)-Phe(4-O-Bzl)-Tyr-NH₂;
(T)aeg-cyclo(D-Cys-Pal-D-Trp-Lys-Cys)-A5c-Tyr-NH₂;
(T)aeg-cyclo(D-Cys-Pal-D-Trp-Lys-Cys)-Abu-Tyr-NH₂;
D-Cpa-cyclo(D-Cys-(T)aeg-D-Trp-Lys-Cys)-Thr(Bzl)-Tyr-NH₂;

(C)aeg-c(D-Cys-Pal-D-Trp-Lys-D-Cys)-Thr(Bzl)-Tyr-NH$_2$:
D-Cpa-c(D-Cys-Pal-D-Trp-Lys-D-Cys)Thr(Bzl)-Tyr-NH$_2$;
(T)aeg-c(Pen-Pal-D-Trp-Lys-D-Cys)Thr(Bzl)-Tyr-N H$_2$;
(T)aeg-c(D-Cys-Trp-D-Trp-Lys-D-Cys)Thr(Bzl)-Tyr-NH$_2$;
(T)aeg-c(D-Cys-Phe-D-Trp-Lys-D-Cys)Thr(Bzl)-Tyr-N H$_2$;
(T)aeg-c(D-Cys-Pal-D-Trp-Orn-D-Cys)Thr(Bzl)-Tyr-NH$_2$;
(T)aeg-c(D-Cys-Pal-D-Trp-hLys-D-Cys)Thr(Bzl)-Tyr-NH$_2$;
(T)aeg-c(D-Cys-Pal-D-Trp-lamp-D-Cys)Thr(Bzl)-Tyr-NH$_2$;
(T)aeg-c(D-Cys-Pal-D-Trp-Cha(4-am)-D-Cys)Thr(Bzl)-Tyr-NH$_2$;
(T)aeg-c(D-Cys-Pal-Trp-Lys-D-Cys)-Ser(Bzl)-Tyr-NH$_2$:
(T)aeg-c(D-Cys-Pal-D-Trp-Lys-Cys)Thr(Bzl)D-Tyr-NH$_2$;
(T)aeg-c(D-Cys-Pal-D-Trp-Lys-D-Cys)Thr(Bzl)-Trp-NH$_2$;
(T)aeg-c(D-Cys-Pal-D-Trp-Lys-D-Pen)Thr(Bzl)-Tyr-NH$_2$;
(C)aeg-c(D-Cys-Phe-D-Trp-Lys-D-Cys)Thr(Bzl)-Tyr-NH$_2$;
Ina-c(D-Cys-Phe-D-Trp-Lys-D-Cys)-Thr(Bzl)-Tyr-NH$_2$;
Mnf-c(D-Cys-Phe-D-Trp-Lys-D-Cys)-Thr(Bzl)-Tyr-NH$_2$;
Inp-c(D-Cys-Phe-D-Trp-Lys-D-Cys)-Thr(Bzl)-Tyr-NH$_2$:
Nua-c(D-Cys-Phe-D-Trp-Lys-D-Cys)-Thr(Bzl)-Tyr-NH$_2$;
Pyp-c(D-Cys-Phe-D-Trp-Lys-D-Cys)-Thr(Bzl)-Tyr-NH$_2$;
c(D-Cys-Phe-D-Trp-Lys-D-Cys)-Thr(Bzl)-Tyr-NH$_2$;
(T)aeg-Pal-c(D-Cys-D-Trp-Lys-D-Cys)Thr(Bzl)-Tyr-NH$_2$;
(T)aeg-Pal-c(D-Cys-D-Trp-Lys-D-Cys)Tyr(Bzl)Thr-NH$_2$;
(C)aeg-Phe-c(D-Cys-D-Trp-Lys-D-Cys)Thr(Bzl)-Tyr-NH$_2$;
(T)aeg-D-Trp-c(D-Cys-Pal-Lys-D-Cys)Thr(Bzl)-Leu-NH$_2$;
or a pharmaceutically acceptable salt thereof.

In still yet another most preferred embodiment the invention features a compound according to Formula III, wherein said compound is of the formula:
Hca-cyclo(D-Cys-Tyr-D-Trp-Lys-Cys)-Nal-NH$_2$;
Ac-Nal-cyclo(D-Cys-Tyr-D-Trp-Lys-Cys)-Nal-NH$_2$;
Ac-D-Phe-cyclo(D-Cys-Tyr-D-Trp-Lys-Cys)-Nal-NH$_2$;
Ac-D-Nal-cyclo(D-Cys-Tyr-D-Trp-Lys-Cys)-Nal-NH$_2$;
D-Phe-cyclo(D-Cys-Tyr-D-Trp-Lys-Cys)-N al-N H$_2$;
Nal-cyclo(D-Cys-Tyr-D-Trp-Lys-Cys)-Nal-NH$_2$;
D-Nal-cyclo(D-Cys-Tyr-D-Trp-Lys-Cys)-Nal-NH$_2$;
D-Phe-cyclo(Cys-Tyr-D-Trp-Lys-Cys)-Thr-NH$_2$;
D-4-NO$_2$-Phe-cyclo(D-Cys-Tyr-D-Trp-Lys-Cys)-Nal-NH$_2$:
Ac-D-4-NO$_2$-Phe-cyclo(D-Cys-Tyr-D-Trp-Lys-Cys)-Nal-NH$_2$;
D-4-NO$_2$-Phe-Pal-cyclo(D-Cys-Phe(4-O-Bzl)-D-Trp-Lys-Cys)-Tyr-NH$_2$;
D-4-NO$_2$-Phe-cyclo(D-Cys-Pal-D-Trp-Lys-Cys)-Thr(Bzl)-Tyr-NH$_2$;
Cpa-cyclo(D-Cys-Pal-D-Trp-Lys-Cys)-Thr(Bzl)-Tyr-NH$_2$;
D-4-NO$_2$-Phe-cyclo(D-Cys-Pal-D-Trp-Lys-Cys)-Thr(Bzl)-NH$_2$;
D-4-NO$_2$-Phe-cyclo(D-Cys-Pal-D-Trp-Lys-D-Cys)-Thr(Bzl)-Tyr-NH$_2$;
D-4-NO$_2$-Phe-cyclo(D-Cys-Tyr-D-Trp-Lys-Cys)-Thr(Bzl)-Tyr-NH$_2$;
4-NO$_2$-Phe-cyclo(D-Cys-Pal-D-Trp-Lys-Cys)-Thr(Bzl)-Tyr-NH$_2$;
D-Nal-cyclo(D-Cys-Pal-D-Trp-Lys-Cys)-Thr(Bzl)-Tyr-NH$_2$;
Pro-cyclo(D-Cys-Pal-D-Trp-Lys-Cys)-Thr(Bzl)-Tyr-NH$_2$;
Cpa-cyclo(D-Cys-Pal-D-Trp-Lys-Cys)-Thr(Bzl)-Nal-NH$_2$;
Ser(Bzl)-cyclo(D-Cys-Pal-D-Trp-Lys-Cys)-Thr-Tyr-NH$_2$;
(T)aeg-cyclo(D-Cys-Pal-D-Trp-Lys-Cys)-Thr(Bzl)-Tyr-N H$_2$;
(C)aeg-cyclo(D-Cys-Pal-D-Trp-Lys-Cys)-Thr(Bzl)-Tyr-NH$_2$;
Aic-cyclo(D-Cys-Pal-D-Trp-Lys-Cys)-Thr(Bzl)-Tyr-NH$_2$;
(C(z))aeg-cyclo(D-Cys-Pal-D-Trp-Lys-Cys)-Thr(Bzl)-Tyr-NH$_2$;
(A(z))aeg-cyclo(D-Cys-Pal-D-Trp-Lys-Cys)-Thr(Bzl)-Tyr-NH$_2$;
(T)aeg-cyclo(D-Cys-Pal-D-Trp-Lys-D-Cys)-Thr(Bzl)-Tyr-NH$_2$;
(A)aeg-cyclo(D-Cys-Pal-D-Trp-Lys-Cys)-Thr(Bzl)-Tyr-NH$_2$;
(G)aeg-cyclo(D-Cys-Pal-D-Trp-Lys-Cys)-Thr(Bzl)-Tyr-NH$_2$;
(T)aeg-cyclo(D-Cys-4-Pal-D-Trp-Lys-Cys)-Thr(Bzl)-Tyr-NH$_2$;
(T)aeg-cyclo(D-Cys-Tyr-D-Trp-Lys-Cys)-Thr(Bzl)-Tyr-NH$_2$;
(T)aeg-cyclo(D-Cys-Phe-D-Trp-Lys-Cys)-Thr(Bzl)-Tyr-NH$_2$;
(T)aeg-cyclo(D-Cys-(T)aeg-D-Trp-Lys-Cys)-Thr(Bzl)-Tyr-NH$_2$:
(T)aeg-cyclo(D-Cys-Pal-D-Trp-Lys-Cys)Ser(Bzl)-Tyr-NH$_2$;
(T)aeg-cyclo(D-Cys-Pal-D-Trp-Lys-Cys)-Phe(4-O-Bzl)-Tyr-N H$_2$;
(T)aeg-cyclo(D-Cys-Pal-D-Trp-Lys-Cys)-A5c-Tyr-N H$_2$;
(T)aeg-cyclo(D-Cys-Pal-D-Trp-Lys-Cys)-Abu-Tyr-NH$_2$;
D-Cpa-cyclo(D-Cys-(T)aeg-D-Trp-Lys-Cys)-Thr(Bzl)-Tyr-NH$_2$;
(T)aeg-cyclo(D-Cys-Pal-D-Trp-Lys-D-Cys)-Thr(Bzl)-p-Me-Phe-NH$_2$;
Ac-(T)aeg-cyclo(D-Cys-Pal-D-Trp-Lys-D-Cys)-Thr(Bzl)-Tyr-NH$_2$;
(T)aeg-cyclo(D-Cys-Pal-D-Trp-Lys-D-Cys)-Nal-NH$_2$;
D-Cpa-cyclo(D-Cys-Pal-D-Trp-Lys-D-Cys)Nal-NH$_2$;
(A)aeg-cyclo(D-Cys-Pal-D-Trp-Lys-D-Cys)-Thr(Bzl)-Tyr-NH$_2$; or
(C)aeg-cyclo(D-Cys-Pal-D-Trp-Lys-D-Cys)-Thr(Bzl)-Tyr-NH$_2$;

or a pharmaceutically acceptable salt thereof.

In still another most preferred embodiment the invention features a compound according to Formula IV, wherein said compound is of the formula:

cyclo(Trp-D-Trp-Lys-Phe(4-O-Bzl)-Phe-T)aeg);
cyclo(Trp-D-Trp-Lys-Pal-Phe-(T)aeg); or
cyclo(Phe-Phe-D-Trp-Lys-Thr-(T)aeg);

or a pharmaceutically acceptable salt thereof.

Preparation of Peptides

Peptides were synthesized on Rink Amide MBHA resin, (4-(2',4'-dimethoxyphenyl-Fmoc-aminomethyl)-phenoxyacetamido-norleucyl-MBHA resin), using a standard solid phase protocol of FMOC chemistry and cleaved with a TFA/Phenol/H$_2$O/triisoproylsilane (83 ml/5 g/10 ml/2 ml) mixture. Peptides were cyclized in CH$_3$CN/H$_2$O (5 ml/5 ml) using EKATHIOX™ resin (EKAGEN Corporation, San Carlos, Calif.) and purified on C$_{18}$ silica (Rainin Instruments Co., Woburn, Mass., now Varian Analytical, Walnut Creek, Calif.), using acetonitrile/0.1% trifluoroacefic acid buffers. Homogeneity was assessed by analytical HPLC and mass spectrometry and was determined to be >95% for each peptide.

Peptides having general structure

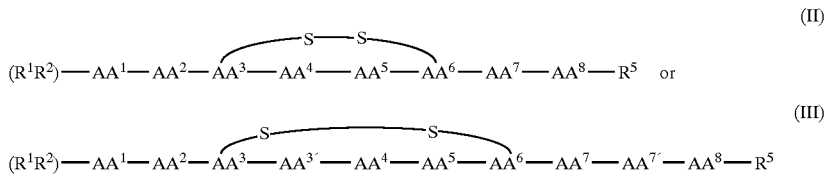

that is, having a cyclic tetra- or pentapeptyl backbone, were synthesized on Rink Amide MBHA resin, (4-(2',4'-dimethoxyphenyl-Fmoc-aminomethyl)-phenoxyacetamidonor-leucyl-MBHA resin), following a standard solid phase protocol of Fmoc-chemistry until the desired peptide was assembled. Final cleavage/deprotection was achieved by the treatment of the peptide-resin with a cocktail of TFA/Phenole/H$_2$O/Triisopropylsilane (83:5:10:2 mL/g/mL/ml.

Cyclization (S—S bond formation) was achieved by dissolving the linear peptide in a 50% mixture of CH$_3$CN/H$_2$O, except where otherwise indicated, followed by the addition of 2.5 eq. of EKATHIOX resin then stirring overnight.

Peptides were purified on C$_{18}$ silica column using acetonitrile/0.1% TFA buffer. Homogeneity was assessed by analytical HPLC and MAS spectrometry and was determined to be >95% for each peptide except where otherwise indicated.

Peptides having a carboxylic function at their C-Terminal were synthesized on Wang resin (p-Benzyloxybenzyl Alcohol resin), cleaved from resin and deprotected by cocktail B (TFA:Phenole:H$_2$O:Triisopropylsilane in the ratio 88:5:5:2).

Head-To-Tail cyclic peptides having the general structure of

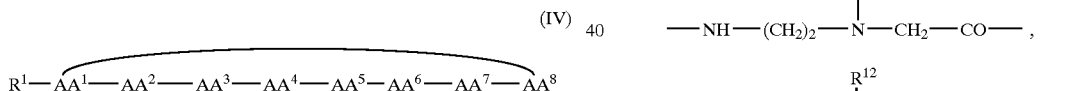

were synthesized first as a totally protected linear peptide on 2-chlorotrityl chloride resin.

The first Fmoc deprotection was carried out using 5% piperidine in DMF/DCM (1:1) for about 10 minutes followed by 25% piperidine in DMF for about 15 minutes. All subsequent deprotections were performed using a standard solid phase protocol of FMOC chemistry.

Protected linear peptides were obtained by treating the resin with acetic acid/TFE/DCM (1:1:8 by vol.) for about 60 minutes at room temperature.

Head-to-tail cyclization was achieved using HATU/HOAT/DIPEA as the coupling/cyclization reagent The all-protected cyclic peptide was treated with a cocktail of TFA/Phenole/H$_2$O/Triisopropylsilane (83:5:10:2 mL/g/mL/mL) for about 2½ hours to achieve final deprotection.

Peptides were purified on C$_{18}$ silica column using acetonitrile/0.1% TFA buffer as eluant. Homogeneity was assessed by analytical HPLC and MAS spectrometry and was determined to be>97% pure for each peptide.

As noted above, certain compounds of the invention incorporate one or more of the amino acid moiety R$^{11}$, having the structure

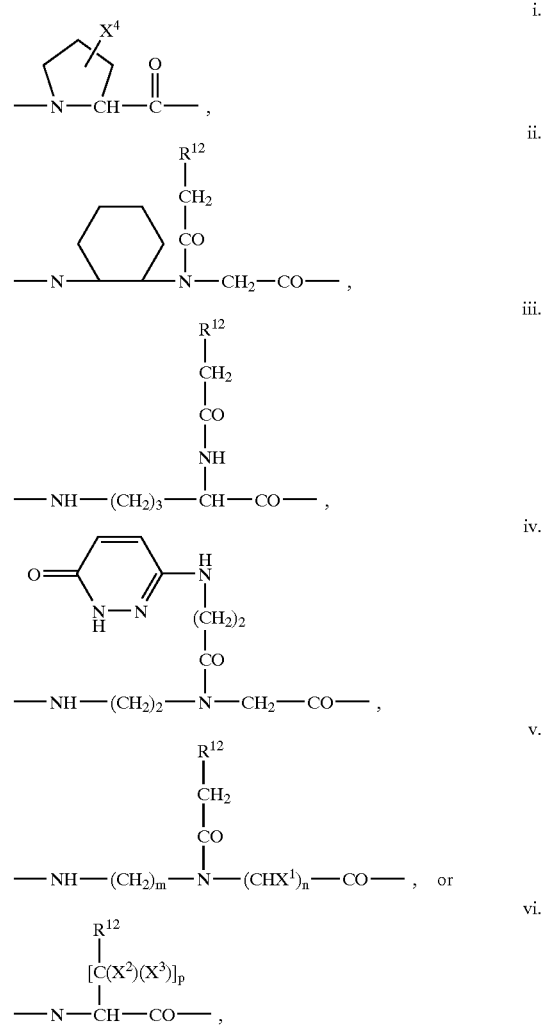

wherein R$^{12}$, X$^1$, X$^2$, X$^3$, X$^4$, m, n, and p each is as defined in the claims. It will be apparent to one skilled in the art of chemical synthesis that the various R$^{11}$ amino acids may be readily synthesized using appropriate starting materials and known synthesis procedures. Examples of pertinent procedures may be found in the following publications, hereby incorporated by reference: aminoethylglycine: Tetrahedron, vol. 51, pp. 6179 (1995); Bioorganic & Medicinal Chemistry Letters, vol 5, No. 11, p. 1159 (1995); Tetrahedron, vol. 53, no. 43, p. 14671 (1997); Nucleosides, Nucleotides, vol. 16 (10 & 11), p. 1893 (1997); α-α-dialkylated amino acid with nucleobase side chain, Proc. Natl. Acad. Sci. USA, vo. 92, p. 12013 (1995); aminocyclohexylglycine, Chem. Eur. J. vol. 3. No. 6, p. 912 (1997); α-N-Boc-α-N-(thymin-1- ylacetyl)ornithine, Bioorganic & Medicinal Chemistry Letters, vol. 6, no. 7, p. 793 (1996); substituted proline, J. Chem. Soc. Perkin. Trans., vol 1, pp. 539, 547, 555 (1997); N-(aminomethyl)-β-alanine, Tetrahedron Left., vol. 36, No. 38, p. 6941 (1995); substituted ornithine, Nucleosides & Nucleotides, vol 17 (1–3), pp. 219, 339 (1998); structure vi., Tetrahedron Left., Vol. 36, no 10, p. 1713 (1995); Tetrahedron Lett, Vol. 38, no 48, p. 8363 (1997); structure v., Tetrahedron Left., Vol 39, p. 4707 (1998); compound iv., J. Amer. Chem. Soc., vol. 119, p. 11116 (1997); aminoproline, Bioorganic & Medicinal Chemistry Left., vol. 7, no. 6, p. 681 (1997); chiral polynucleic acid, Tetrahedron Lett., vol. 35, no. 29, p. 5173 (1994); Bioorganic & Medicinal Chemistry Lett., vol. 4, no. 8, p. 1077 (1994).

Below is a detailed description regarding the synthesis of Analog #1. Other peptides of the invention can be prepared by making appropriate modifications, within the ability of someone of ordinary skill in the art of peptide synthesis.

Step 1: Preparation of Fmoc-Nal-O-tert-Butyl-Tyr-S-trityl-D-Cys-N-in-t-Boc-D-Trp-N-ε-t-Boc-Lys-S-trityl-D-Cys-Abu-Nal-4-(2',4'-Dimethoxphenylamino methyl) phenoxyacetamido-norluacyl-4-methylbenzhydrylamine resin.

Rink amide MBHA resin (Novabiochem, Inc., San Diego, Calif.), 1 g, (0.53 mmole), was placed in reaction vessel #1 (RV-1) of a Model 90 peptide synthesizer, (Advanced ChemTech, Louisville, Ky.). The peptide synthesizer was programmed to perform the following reaction cycle:

a. Dimethylformamide;
b. 25% piperidine in dimethylformamide (2 times for 15 minutes each, with 1 time wash with DMF in between);
c. DMF washes (3×10 mL, 1 minute each);

The resin was stirred with FMOC-Nal (2.12 mmol), 2-(1H-benzotriazol-1-yl)-1,1,3,3-tetramethyluronium hexafluorophosphate (HBUT) (2.01 mmole), and diisopropylethyl amino (4.24 mmole) in dimethylformamide for about 1½ hours and the resulting amino acid resin was then cycled through steps (a) to (c) in the above wash program. The Nal-resin was coupled with Fmoc-Abu, then cycled as described above. It was dried under vacuum.

The following amino acids (1.4 mmole) were coupled successively to the peptide resin (0.35 mmole), by the same procedure: Fmoc-S-Trityl-D-Cys, Fmoc-N-ε-t-Boc-Lys, Fmoc-N-in-t-Boc-D-Trp. The peptide resin, after drying under vacuum, was split and one portion coupled with Fmoc-S-Trityl-D-Cys, Fmoc-O-t-butyl-Tyr. The coupled portion was split again and one portion coupled with Fmoc-Nal. After washing with DMF (3×10 mL, 1 minute each) and drying under vacuum, the completed resin weighed 0.242 g.

Step 2: Preparation of H-Nal-Tyr-D-Cys-D-Trp-Lys-D-Cys-Abu-Nal-NH₂ The peptide resin obtained from Step 1 (0.24 g, 0.087 mmole) was mixed with a freshly prepared solution of TFA (8.8 mL), phenol (0.5 g), H₂O (0.5 mL) and triisopropylsilane (0.2 mL) at room temperature and stirred for about 2½ hours. Excess TFA was evaporated under reduced pressure to an oily residue. Ether was then added to the oily residue and the free linear peptide was precipitated, filtered, then washed with dry ether. The crude peptide was then dissolved in 11 mL of CH₃CN/H₂O/0.1 N HOAc (5 mL/5 mL/1 mL), followed by the addition of 200 mg EKATHIOX® resin. The mixture was stirred overnight and then filtered. The filtrate was evaporated to a small volume then applied to a column (22–250 mm) of microsorb octadecylsilane silica (5 μm), followed by elution with a linear gradient (30% to 80%, 30 minutes) of acetonitrile in water, in which both solvents have 0.1% trifluoroacetic acid. Fractions were examined by analytical high performance liquid chromatography ("HPLC") and pooled to give maximum purity. Lyophilization of the solutions from water gave 10 mg of the product as a white, fluffy powder. The product was found to be homogeneous by HPLC C₁₈ silica using the same eluant as immediately above, (tR=16.646 minutes). Infusion mass spectrometry confirmed the composition of the cyclic octapeptide; (MW 1178.45).

OTHER EMBODIMENTS

From the above description, one skilled in the art can easily ascertain the essential characteristics of the present invention, and without departing from the spirit and scope thereof, can make various changes and modifications of the invention to adapt it to various uses and conditions. Thus, other embodiments are also within the claims.

What is claimed is:

1. A compound of formula (II):

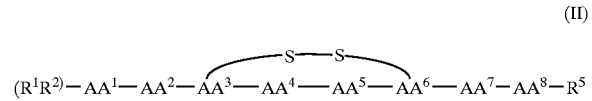

(II)

or a pharmaceutically acceptable salt thereof,
wherein
the α-nitrogen of $AA^1$, $AA^2$, $AA^3$, $AA^4$, $AA^5$, $AA^6$, $AA^7$, and $AA^8$ each is, independently, optionally substituted with $(C_{1-4})$alkyl, $(C_{3-4})$alkenyl, $(C_{3-4})$alkynyl, or $(C_{1-6})$alkyl-C(O)—;

$AA^1$ is absent or the D- or L-isomer of an amino acid selected from the group consisting of $R^{11}$, Aac, Aic, Arg, Asn, Asp, Dip, Gln, Glu, Hyp, Lys, Mac, Macab, Orn, Pip, Pro, Ser, Ser(Bzl), Thr, Thr(Bzl), Pip, hArg, Bip, Bpa, Tic, Cmp, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, I-Iqc, 3-Iqc, C4c, 5-Iqs, Htqa, 4-Mqc, Thn, α-Chpa, Cit, Nua, Pyp and an optionally substituted aromatic α-amino acid,
wherein said optionally substituted aromatic α-amino acid is optionally substituted with one or more substituents selected from the group consisting of halogen, $NO_2$, OH, CN, $(C_{1-6})$alkyl, $(C_{2-6})$alkenyl, $(C_{2-6})$alkynyl, and $NR^9R^{10}$;

$AA^2$ is absent or the D- or L-isomer of an amino acid selected from the group consisting of $R^{11}$, Aic, Arg, Hca, His, Hyp, Pal, $F_5$-Phe, Phe, Pro, Trp, $X^0$-Phe, Pip, hArg, Bip, Bpa, Tic, Cmp, Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, I-Iqc, 3-Iqc, C4c, 5-Iqs, Htqa, 4-Mqc, Thn, α-Chpa, Cit, Nua, and Pyp; $AA^3$ is the D- or L-isomer of an amino acid selected from the group consisting of Cys, hCys, Pen, Tpa and Tmpa;

$AA^4$ is a D- or L-isomer of an amino acid selected from the group consisting of Trp, N-Met-Trp, β-Met-Trp, His, hHis, hArg, Bip, Tic, Htic, Dip, Sala, Aala, Thza, Thia, Bal, Fala, Pala, and an optionally substituted aromatic α-amino acid,
wherein said optionally substituted aromatic α-amino acid is optionally substituted with one or more substituents each independently selected from the group consisting of halogen, $NO_2$, OH, $(C_{1-4})$alkyl, $(C_{2-4})$alkenyl, $(C_{2-4})$alkynyl, Bzl, O-Bzl, and $NR^9R^{10}$;

AA⁵ is a D- or L-isomer of an amino acid selected from the group consisting of 4-Pip-Gly, 4-Pip-Ala, cis-4-Acha, trans-4-Acha, trans-4-Amcha, hLys, Lys, Orn, hArg, Bip, Tic, Htic, Dip, Sala, Aala, Thza, Thia, Bal, Fala, and Pala,
  wherein the side-chain amino group of said amino acid is optionally mono- or di-substituted with $R^3$ and $R^4$;

AA⁶ is a D- or L-isomer of an amino acid selected from the group consisting of Cys, hCys, Pen, Tpa, and Tmpa;

AA⁷ is absent or a D- or L-isomer of an amino acid selected from the group consisting of $R^{11}$, Aic, A3c, A4c, A5c, A6c, Abu, Aib, β-Ala, Arg, Bpa, Cha, Deg, Gaba, His, Ile, Leu, Nal, Nle, Pal, Phe, F₅-Phe, Pro, Sar, Ser, Ser(Bzl), Thr, Thr(Bzl), Trp, N-Me-Art Trp, Val, N-Me-Val, hArg, Bip, Tic, Htic, Dip, Sala, Aala, Thza, Thia, Bal, Fala, Pala, and $X^0$-Phe;

AA⁸ is absent or the D- or L-isomer of an amino acid selected from the group consisting of $R^{11}$, an optionally substituted aromatic α-amino acid, Maa, Maaab, Ser, Ser(Bzl), Thr, Thr(Bzl), Tyr, Phe(4-O-Bzl), F₅-Phe, and $X^5$-Phe;

$R^1$ and $R^2$ each is, independently, H, E-, $E(O)_2S$—, $E(O)C$—, EOOC—, $R^{13}$, or absent;

$R^3$ and $R^4$ each is, independently, $(C_{1-12})$alkyl, $(C_{2-12})$alkenyl, $(C_{2-12})$alkynyl, phenyl, naphthyl, phenyl-$(C_{1-6})$alkyl, phenyl-$(C_{2-6})$alkenyl, phenyl-$(C_{2-6})$alkynyl, naphthyl-$(C_{1-6})$alkyl, naphthyl-$(C_{2-6})$alkenyl, naphthyl-$(C_{2-6})$alkynyl, (cyclo$(C_{3-7})$alkyl)-$(c_{1-6})$alkyl, (cyclo$(C_{3-7})$alkyl)-$(C_{2-6})$alkenyl, (cyclo$(C_{3-7})$alkyl)-$(c_{2-6})$alkynyl, heterocyclyl-$(C_{1-4})$alkyl, heterocyclyl-$(C_{2-4})$alkenyl, heterocyclyl-$(C_{2-4})$alkynyl, 1-adamantyl, 2-adamantyl, 9-fluorenylmethyl, dicyclopropylmethyl, dimethylcyclopropylmethyl, or benzhydryl;

$R^5$ is —$OR^6$, —$NR^7R^8$, or absent,
  wherein each $R^6$, $R^7$ and $R^8$ is, independently, H, $(C_{1-12})$alkyl, $(C_{2-12})$alkenyl, $(C_{2-12})$alkynyl, phenyl, naphthyl, phenyl-$(C_{1-6})$alkyl, phenyl-$(C_{2-6})$alkenyl, phenyl-$(C_{2-6})$alkynyl, naphthyl-$(C_{1-6})$alkyl, naphthyl-$(C_{2-6})$alkenyl, naphthyl-$(C_{2-6})$alkynyl, 1-adamantyl, 2-adamantyl, 9-fluorenylmethyl, dicyclopropylmethyl, dimethylcyclopropylmethyl, or benzhydryl;

$R^9$ and $R^{10}$ each is, independently, H, $(C_{1-6})$alkyl, $(C_{3-4})$alkenyl, $(C_{3-4})$alkynyl, 1-adamantyl, or 2-adamantyl;

$R^{11}$ is, independently for each occurrence, a D- or L-amino acid of the formula:

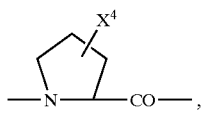  (1)

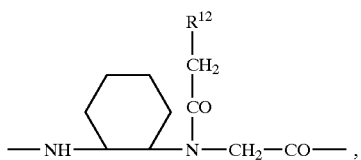  (2)

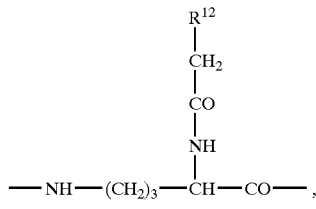  (3)

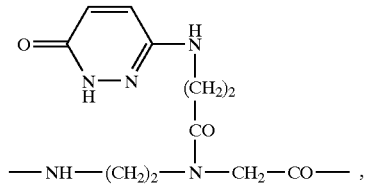  (4)

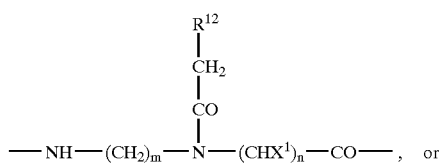  (5)

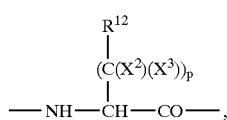  (6)

wherein m and n each is, independently, 1, 2, or 3, and p is 0, 1, or 2;

$R^{12}$ is, independently for each occurrence, an optionally substituted moiety of the formula:

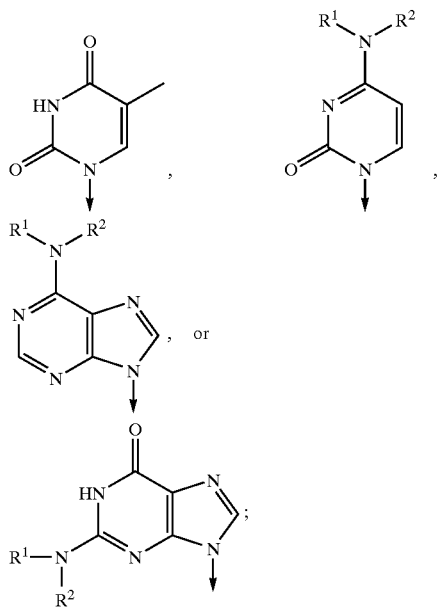

$R^{13}$ is a moiety according to the formula

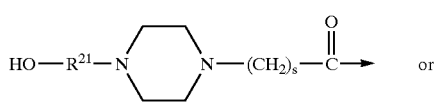 or

-continued

HO—$R^{21}$—N⟨ ⟩N—$(CH_2)_s$—S(=O)(=O)— ,    5 wherein $R^{21}$ is $(C_{1-4})$alkyl and s is 1, 2, 3, or 4;
E is, independently for each occurrence, an optionally substituted moiety selected from the group consisting of $(C_{1-12})$alkyl, $(C_{2-12})$alkenyl, $(C_{2-12})$alkynyl, phenyl, naphthyl, phenyl-$(_{1-6})$alkyl, phenyl-$(C_{2-6})$alkenyl, phenyl-$(C_{2-6})$alkynyl, naphthyl-$(C_{1-6})$alkyl, naphthyl-$(C_{2-6})$alkenyl, naphthyl-$(C_{2-6})$alkynyl, (cyclo$(C_{3-7})$alkyl)-$(C_{1-6})$alkyl, (cyclo$(C_{3-7})$alkyl)-$(C_{2-6})$alkenyl, (cyclo$(C_{3-7})$alkyl)-$(C_{2-6})$alkynyl, heterocyclyl-$(C_{1-4})$ alkyl, heterocyclyl-$(C_{2-4})$alkenyl, heterocyclyl-$(C_{2-4})$alkynyl, 1-adamantyl, 2-adamantyl, dicyclopropylmethyl, dimethylcyclopropylmethyl, 9-fluorenylmethyl, and benzhydryl;
wherein the optionally substituted moiety defined for E is optionally substituted with one or more substituents each independently selected from the group consisting of halogen, OH, Bzl, O-Bzl, $NO_2$, CN, COOH, and SH;
$X^0$ is halogen, $NO_2$, $CH_3$, OH, Bzl, O-Bzl or CN;
$X^1$ is H, $(C_{1-6})$alkyl, $(C_{2-6})$alkenyl, $(C_{2-6})$alkynyl, indolyl, imidazolyl, 1-naphthyl, 3-pyridyl, optionally ring-substituted benzyl, or a moiety which corresponds to the side-chain group of Arg, Leu, Gln, Lys, Tyr, His, Thr, Trp, Phe, Val, Ala, Lys, or His;
wherein said optionally ring-substituted benzyl is optionally substituted with one or more substituents selected from the group consisting of halogen, OH, $(C_{1-6})$alkoxy, mono- or di-$(C_{1-6})$alkylamino, $(C_{1-4})$alkyl, $(C_{2-4})$alkenyl, $(C_{2-4})$alkynyl, and $N^9R^{10}$;
$X^2$ and $X^3$ each is, independently, H, halogen, OH, =O, =S, $(c_{1-12})$alkyl, $(C_{2-12})$alkenyl, $(C_{2-12})$alkynyl, phenyl, naphthyl, phenyl-$(C_{1-6})$alkyl, phenyl-$(C_{2-6})$alkenyl, phenyl-$(C_{2-6})$alkynyl, naphthyl-$(C_{1-6})$alkyl, naphthyl-$(C_{2-6})$alkenyl, naphthyl-$(C_{2-6})$alkynyl, (cyclo$(C_{3-7})$alkyl)-$(C_{1-6})$alkyl, (cyclo$(C_{3-7})$alkyl)-$(C_{2-6})$alkenyl, (cyclo$(C_{3-7})$alkyl)-$(C_{2-6})$alkynyl, heterocyclyl-$(C_{1-4})$alkyl, heterocyclyl-$(C_{2-4})$alkenyl, heterocyclyl-$(C_{2-4})$alkynyl, 1-adamantyl, 2-adamantyl, dicyclopropylmethyl, or dimethylcyclopropyl methyl;
$X^4$ is H, OH, or $NH_2$; and
$X^5$ is halogen, $NO_2$, $CH_3$, OH, Bzl or O-Bzl;
provided that:
at least one of $AA^7$ or $AA^8$ is present;
at least six amino acid residues are present;
when $AA^1$ is a D- or L-isomer of an amino acid selected from the group consisting of Mac or Macab, then $AA^8$ is a D- or L-isomer of an amino acid selected from the group consisting of Maa and Maaab, and when $AA^8$ is a D- or L-isomer of an amino acid selected from the group consisting of Maa and Maaab, then $AA^1$ is a D- or L-isomer of Mac or of Macab, and $AA^1$ is connected by a disulfide bond with $AA^8$;
$AA^2$ can be D- or L-Hca only when $AA^1$ is absent;
when one of $R^1$ or $R^2$ is $E(O)_2S$—, E(O)C—, EOOC—, or $R^{13}$, the other is H;
when $R^5$ is absent, then one of $R^1$ or $R^2$ is also absent, and the N-terminal amino acid and C-terminal amino acid together form an amide bond;
when one of $X^2$ or $X^3$ is C=O or C=S, the other is absent; and
said compound of formula (I) is not of the formula:
D-4-$NO_2$-Phe-Phe(4-O-Bzl)-cyclo(D-Cys-D-Trp-Lys-Cys)Cha-Nal-$NH_2$; or
D-4-$NO_2$-Phe-cyclo(D-Cys-Phe(4-O-Bzl)-D-Trp-Lys-Cys)-Val-Tyr-$NH_2$.

2. A compound of formula (III):

(III)

$(R^1R^2)$—$AA^1$—$AA^2$—$AA^3$—$AA^{3b}$—$AA^4$—$AA^5$—$AA^6$—$AA^7$—$AA^{7b}$—$AA^8$—$R^5$ (with S—S disulfide bridge between $AA^3$ and $AA^6$)

or a pharmaceutically acceptable salt thereof, wherein
$AA^1$ is absent or the D- or L-isomer of an amino acid selected from the group consisting of $R^{11}$, Aac, Aic, Arg, Asn, Asp, Gln, Glu, Hca, His, Hyp, Lys, Mac, Macab, Orn, Pro, Ser, Ser(Bzl), Thr, Thr(Bzl), Pip, hArg, Bip, Bpa, Tic, Cmp, Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, I-Iqc, 3-Iqc, C4c, 5-Iqs, Htqa, 4-Mqc, Thn, α-Chpa, Cit, Nua, Pyp and an optionally substituted aromatic α-amino acid,
wherein said optionally substituted aromatic α-amino acid is optionally substituted with one or more substituents selected from the group consisting of halogen, $NO_2$, OH, CN, $(C_{1-6})$alkyl, $(C_{2-6})$alkenyl, $(C_{2-6})$alkynyl, and $NR^9R^{10}$;
$AA^3$ is a D- or L-isomer of an amino acid selected from the group consisting of Cys, hCys, Pen, Tpa, and Tmpa;
$AA^{3b}$ is the D- or L-isomer of an amino acid selected from the group consisting of $R^{11}$, Arg, Bpa, $F_5$-Phe, His, Nal, Pal, 4-Pal, Phe, Trp, hArg, Bip, Tic, Htic, Dip, Sala, Aala, Thza, Thia, Bal, Fala, Pala, and Xs-Phe;
$AA^4$ is a D- or L-isomer of an amino acid selected from the group consisting of Trp, N-Met-Trp, β-Met-Trp, His, hHis, hArg, Bip, Tic, Htic, Dip, Sala, Aala, Thza, Thia, Bal, Fala, Pala, and an optionally substituted aromatic α-amino acid;
wherein said optionally substituted aromatic α-amino acid is optionally substituted with one or more substituents each independently selected from the group consisting of halogen, $NO_2$, OH, CN, $(C_{1-4})$alkyl, $(C_{2-4})$alkenyl, $(C_{2-4})$alkynyl, Bzl, O-Bzl, and $NR^9R^{10}$;
$AA^5$ is a D- or L-isomer of an amino acid selected from the group consisting of 4-Pip-Gly, 4-Pip-Ala, cis-4-Acha, trans-4-Acha, trans-4-Amcha, hLys, Lys, and Orn, and, hArg, Sip, Tic, Htic, Dip, Sala, Aala, Thza, Thia, Bal, Fala, and Pala,
wherein the side-chain amino group of said amino acid is optionally mono- or di-substituted with $R^3$ and $R^4$;
$AA^6$ is a D- or L-isomer of an amino acid selected from the group consisting of Cys, hCys, Pen, Tpa, and Tmpa;
$AA^7$ is absent or a D- or L-isomer of an amino acid selected from the group consisting of $R^{11}$, Aic, A3c, A4c, A5c, A6c, Abu, Aib, β-Ala, Arg, Bpa, Cha, Deg, Gaba, His, Ile, Leu, Nal, Nle, Pal, Phe, Fs-Phe, Pro, Sar, Ser, Ser(Bzl), Thr, Thr(Bzl), Trp, N-Me-Trp, Val, N-Me-Val, hArg, Bip, Tic, Htic, Dip, Sala, Aala, Thza, Thia, Bal, Fala, Pala, and $X^0$-Phe;

$X^0$ is halogen, $NO_2$, $CH_3$, OH, CN, Bzl or O-Bzl;

$R^1$ and $R^2$ each is, independently, H, E-, $E(O)_2S—$, $E(O)C—$, EOOC—, $R^{13}$, or absent;

$R^5$ is —$OR^6$ or —$NR^7R^8$;

$R^{13}$ is a moiety of the formula

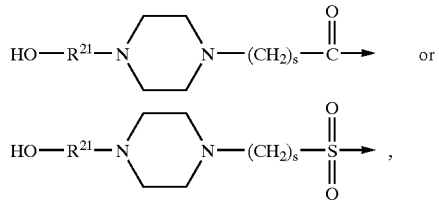

wherein $R^{21}$ is $(C_{1-4})$alkyl and s is 1, 2, 3, or 4;
provided that:
at least one of $AA^1$ or $AA^2$ is present;
when $AA^1$ is a D- or L-isomer of Pro, Hyp, Arg, Pip, hArg, Bip, Bpa, Tic, Cmp, Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, I-Iqc, 3-Iqc, C4c, 5-Iqs, Htqa, 4-Mqc, Thn, α-Chpa, Cit, Nua, Pyp or His, $AA^2$ cannot be a D- or L-isomer of Pro, Hyp, Arg, Pip, hArg, Bip, Bpa, Tic, Cmp, Inc, Inp, Nip, Ppc, Htic, Thi, Tra, Cmpi, Tpr, Iia, Alla, Aba, Gba, Car, Ipa, Iaa, Inip, Apa, Mim, Thnc, Sala, Aala, Thza, Thia, Bal, Fala, Pala, Dap, Agly, Pgly, Ina, Dipa, Mnf, Inic, I-Iqc, 3-Iqc, C4c, 5-Iqs, Htqa, 4-Mqc, Thn, α-Chpa, Cit, Nua, Pyp or His;

when $AA^7$ is a D- or L-isomer of Thr or of Ser, $AA^8$ cannot be a D- or L-isomer of Thr or of Ser;

at least one of $AA^1$, $AA^2$, $AA^{3b}$, $AA^7$, $AA^{7b}$, or $AA^8$ is the D- or L-isomer of $R^{11}$; and when one of $X^2$ or $X^3$ is =O or =S, the other is absent;

or a pharmaceutically acceptable salt thereof.

3. A compound of formula (IV):

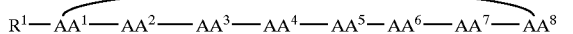

(IV)

wherein $AA^1$ is absent or the D- or L-isomer of an amino acid selected from the group consisting of $R^{11}$, Aic, Hyp, Pro, Ser, Ser(Bzl), Thr, Thr(Bzl), Tic, Htic, Fala and an optionally substituted aromatic α-amino acid;
wherein said optionally substituted aromatic α-amino acid is optionally substituted with one or more substituents each independently selected from the group consisting of halogen, $NO_2$, OH, CN, $(C_{1-6})$alkyl, $(C_{2-6})$alkenyl, $(C_{2-6})$alkynyl, $(C_{1-6})$alkoxy, Bzl, O-Bzl, and $NR^9R^{10}$;

$AA^2$ is absent or the D- or L-isomer of an amino acid selected from the group consisting of $R^{11}$, Arg, $F_5$-Phe, His, Pal, Phe, Trp, hArg, Pala, Bal, Fala, Sala and $X^0$-Phe;

$AA^3$ is the D- or L-isomer of an optionally substituted aromatic α-amino acid,
wherein said optionally substituted aromatic α-amino acid is optionally substituted with one or more substituents selected from the group consisting of halogen, $NO_2$, OH, CN, $(C_{1-4})$alkyl, $(C_{2-4})$alkenyl, $(C_{2-4})$alkynyl, Bzl, O-Bzl, and $NR^9R^{10}$;

$AA^4$ is a D- or L-isomer of an optionally substituted amino acid selected from the group consisting of Trp, N-Met-Trp, β-Me-Trp, Lys, Orn, hLys, cis-4-Acha, trans-4-Acha, trans-4-Amcha, 4-Pip-Gly, 4-Pip-Ala, hArg, Bip, Tic, Htic, Dip, Sala, Aala, Thza, Thia, Bal, Fala, and Pala;
wherein the side chain amino group of said optionally substituted amino acid is optionally substituted with $R^3$ and $R^4$;

$AA^5$ is absent or a D- or L-isomer of $R^{11}$, A3c, A4c, A5c, A6c, Abu, Aib, Aic, β-Ala, Bpa, Cha, Deg, Fs-Phe, Gaba, Ile, Leu, Nal, Nle, Pal, Phe, Pro, Sar, Ser, Ser(Bzl), Thr, Thr(Bzl), Trp, N-Me-Trp, Val, N-Me-Val, hArg, Bip, Tic, Htic, Dip, Sala, Aala, Thza, Thia, Bal, Fala, Pala, or $X^0$-Phe;

$AA^6$ is absent, the D- or L-isomer of $R^{11}$, an aromatic α-amino acid, Fs-Phe, Phe, Thr, Thr(Bzl), Ser, Ser (Bzl), or $X^0$-Phe;

$AA^7$ is absent, the D- or L-isomer of $R^{11}$ or the D- or L-isomer of an aromatic α-amino acid;

$AA^8$ is a D- or L- isomer of $R^{11}$;

$R^1$ is H, E-, $E(O)_2S—$, $E(O)C—$, EOOC—, or $R^{13}$;

$R^{13}$ is a moiety of the formula

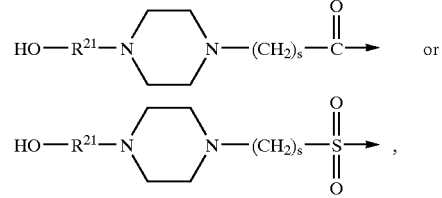

wherein $R^{21}$ is $(C_{1-4})$alkyl and s is 1, 2, 3, or 4;

$X^0$ in the definition of $AA^2$ and $AA^5$ is halogen, $NO_2$, OH, $(C_{1-6})$alkyl, $(C_{1-6})$alkoxy, mono- or di-$(C_{1-6})$alkylamino, Bzl or O-Bzl;

$X^0$ in the definition of $AA^6$ is halogen, $NO_2$, OH, $(C_{1-6})$alkyl, $(C_{1-6})$alkoxy, mono- or di-$(C_{1-6})$alkylamino, Bzl, O-Bzl, or $NR^9R^{10}$; provided that:
at least one of $AA^1$ or $AA^2$ is present;
when $AA^1$ is absent, $AA^2$ and $AA^8$ together form a bond; and
at least two of $AA^5$, $AA^6$, and $AA^7$ are present;
or a pharmaceutically acceptable salt thereof.

4. A compound according to claim 1, wherein
$AA^1$ is absent, Ac-D-Phe, or the D- or L- isomer of $R^{11}$, Pip, Pro, or Ser, or of an aromatic α-amino acid selected from the group consisting of Cpa, Dip, Nal, Pal, and Phe;

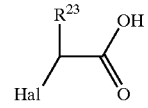

$AA^2$ is absent, Aic, Pal, Phe, Fs-Phe, 4-$NO_2$-Phe, Trp, Tyr, Phe(4-O-Bzl)

AA³ is the D- or L- isomer of an amino acid selected from the

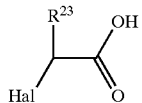

group consisting of Pen, Cys, hCys and Tmpa;
AA⁴ is the D- or L-isomer of Trp, His, N-Me-Trp, β-Me-Trp, hTrp, or hHis;
AA⁵ is Lys, hLys, N-Me-Lys, Orn, cis-4-Acha or 4-Pip-Ala;
AA⁶ is the D- or L-isomer of an amino acid selected from the group consisting of Cys, hCys, Pen and Tmpa;
AA⁷ is A3c, A4c, A5c, A6c, Abu, Aic, β-Ala, Gaba, Nle, Fs-Phe, Phe, Pro, Sar, Ser, Thr, Thr(Bzl), Tyr, Val or absent; and
AA⁸ is R¹¹, Nal, Thr, Thr(Bzl), Tyr, Phe(4-O-Bzl), or absent;
or a pharmaceutically acceptable salt thereof.

5. A compound according to claim 4, wherein
AA¹ is absent or the D- or L- isomer of R¹¹, Pip or Pro, or of an aromatic α-amino acid selected from the group consisting of Cpa, Dip, Nal, Pal, Phe, and Ac-Phe;
AA² is Tyr, Pal, Phe, 4-NO₂-Phe, Trp, or absent;
AA³ is a D- or L-isomer of Cys or Pen;
AA⁴ is D-Trp;
AA⁵ is Lys, Orn, or cis-4-Acha;
AA⁶ is a D- or L-isomer of Cys or Pen;
AA⁷ is A3c, A4c, A5c, A6c, Abu, Aic, β-Ala, Gaba, Nle, Phe, Pro, Sar, Thr, Thr(Bzl), Tyr, Val, or absent; and
AA⁸ is R¹¹, Thr, Tyr, Nal, or absent;
or a pharmaceutically acceptable salt thereof.

6. A compound according to claim 2, wherein
AA¹ is R¹¹, Aic, Hca, Pro, Ser, Ser(Bzl), Trp, Tyr, or a D- or L-isomer of an aromatic α-amino acid selected from the group consisting of Cpa, Nal, Ac-Nal, Phe, Ac-Phe, 4-NO₂-Phe, and Ac-4-NO₂-Phe;
AA² is Pal, Phe, F₅-Phe, Tyr, or absent;
AA³ is a D- or L-isomer of Cys, hCys, Pen or Tmpa;
AA³ᵇ is Pal, 4-Pal, His, Trp; Tyr, Phe(4-O-Bzl), Phe, or R¹¹;
AA⁴ is a D- or L-isomer of Trp or His;
AA⁵ is Lys, N-Me-Lys, Orn, hLys, cis-4-Acha, or 4-Pip-Ala;
AA⁶ is a D- or L-isomer of Cys, hCys, Pen or Tmpa;
AA⁷ is R¹¹, A4c, A5c, Abu, β-Ala, Gaba, Phe, Fs-Phe, Ser(Bzl), Thr, Thr(Bzl), Phe(4-O-Bzl), or absent;
AA⁷ᵇ is R¹¹, Nal, F₅-Phe, X⁰-Phe or absent, wherein X⁰ is halogen, NO₂, CH₃, OH, Bzl or O-Bzl; and
AA⁸ is R¹¹, Nal, Tyr, Phe(4-O-Bzl), or absent;
or a pharmaceutically acceptable salt thereof.

7. A compound according to claim 6, wherein
AA¹ is R¹¹, Aic, Hca, Pro, Ser(Bzl), or a D- or L-isomer of an aromatic α-amino acid selected from the group consisting of Cpa, Nal, Ac-Nal, Phe, Ac-Phe, 4-NO₂-Phe, and Ac-4-NO₂-Phe;
AA² is Pal, Tyr, or absent;
AA³ is a D- or L-isomer of Cys or Pen;
AA³ᵇ is R¹¹, Pal, 4-Pal, Trp, Tyr, Phe(4-O-Bzl), or Phe, wherein R¹¹ is (T)aeg;

AA⁴ is D-Trp;
AA⁵ is Lys, N-Me-Lys, Orn, or cis-4-Acha;
AA⁶ is a D- or L-isomer of Cys or Pen;
AA⁷ is R¹¹, A5c, Abu, Ser(Bzl), Thr, Thr(Bzl), Phe(4-O-Bzl), Gaba, or absent;
AA⁷ᵇ is Nal, X⁰-Phe or absent; and
AA⁸ is Tyr or absent;
or a pharmaceutically acceptable salt thereof.

8. A compound according to claim 3, wherein
AA¹ is Aic, Hyp, Cpa, D-Cpa, Nal, Pal, Phe, Pro, R¹¹, Tyr or absent;
AA² is Phe, Trp, F₅-Phe, His, Tyr, Phe(4-O-Bzl), or R¹¹;
AA³ is a D-isomer of Trp, His, or Pal;
AA⁴ is Lys, N-Me-Lys, Orn, hLys, cis-4-Acha, or 4-Pip-Ala;
AA⁵ is Pal, Phe(4-O-Bzl), Thr(Bzl), Thr, Sar, Gaba, β-Ala, A4c, A5c, A6c, Abu, Aic or absent;
AA⁶ is Thr, Tyr, Ser, F₅-Phe, Cpa, Nal, or D- or L-Phe;
AA⁷ is Nal, Pal, or absent; and
AA⁸ is R¹¹;
or a pharmaceutically acceptable salt thereof.

9. A compound according to claim 8, wherein
AA¹ is Cpa, Nal, Pal, Phe, Tyr or absent;
AA² is Phe, Tyr, Trp, or R¹¹;
AA³ is D-Trp;
AA⁴ is Lys, N-Me-Lys, or cis-4-Acha;
AA⁵ is Pal, Phe(4-O-Bzl), Aic, Gaba, A5c or absent;
AA⁶ is Thr, Nal, or D- or L-Phe;
AA⁷ is absent; and
AA⁸ is R¹¹;
or a pharmaceutically acceptable salt thereof.

10. A compound according to claim 1, wherein R¹ and R⁵ are absent and the N-terminal amino acid and the C-terminal amino acid together form an amide bond; or a pharmaceutically acceptable salt thereof.

11. A compound according to claim 2, wherein R¹ and R⁵ are absent and the N-terminal amino acid and the C-terminal amino acid together form an amide bond; or a pharmaceutically acceptable salt thereof.

12. A compound according to claim 5, wherein said compound is of the formula:
Ac-D-Phe-Tyr-cyclo(D-Cys-D-Trp-Lys-Cys)-Abu-Thr-NH₂;
Nal-Tyr-cyclo(Cys-D-Trp-Lys-D-Cys)-Val-Nal-NH₂;
Nal-Tyr-cyclo(Cys-D-Trp-Lys-D-Cys)-Abu-Nal-NH₂;
D-Dip-Tyr-cyclo(Cys-D-Trp-Lys-D-Cys)-Abu-Nal-NH₂;
Dip-Tyr-cyclo(D-Cys-D-Trp-Lys-D-Cys)-Abu-Nal-NH₂;
Nal-Tyr-cyclo(D-Cys-D-Trp-Lys-D-Cys)-Abu-Nal-NH₂;
Dip-Tyr-cyclo(D-Cys-D-Trp-Lys-D-Cys)-Val-Nal-NH₂;
Nal-Tyr-cyclo(D-Cys-D-Trp-Lys-D-Cys)-Val-Nal-NH₂;
cyclo(D-Phe-Tyr-cyclo(D-Cys-D-Trp-Lys-Cys)-Abu-Thr);
Cpa-Pal-cyclo(D-Cys-D-Trp-Lys-D-Cys)-A3c-Nal-NH₂;
Cpa-Pal-cyclo(D-Cys-D-Trp-Lys-D-Cys)-A5c-Nal-NH₂;
Cpa-Pal-cyclo(D-Cys-D-Trp-Lys-D-Cys)-A6c-Nal-NH₂;
(G(z))aeg-cyclo(D-Cys-D-Trp-Lys-D-Cys)-A5c-Nal-NH₂;
Pal-cyclo(D-Cys-D-Trp-Lys-D-Cys)-A5c-Nal-NH₂;
Cpa-Pal-cyclo(D-Cys-D-Trp-Lys-D-Cys)-β-Ala-Nal-NH₂;
Cpa-Pal-cyclo(D-Cys-D-Trp-Lys-D-Cys)-Sar-Nal-NH₂;
Cpa-Pal-cyclo(D-Cys-D-Trp-Lys-D-Cys)-Gaba-Nal-NH₂;
Cpa-Pal-cyclo(D-Cys-D-Trp-Lys-D-Cys)-Pro-Nal-NH₂;
Pro-Phe-c(D-Cys-D-Trp-Lys-D-Cys)-Nle-Phe-NH₂;
Pro-Phe-c(D-Cys-D-Trp-Lys-D-Cys)-Thr-Nle-NH₂;
Pro-Phe-c(D-Cys-D-Trp-Lys-D-Cys)-Thr-Phe-NH₂;

Cpa-Phe-c(D-Cys-D-Trp-Lys-D-Cys)-Gaba-NH$_2$;
Cpa-Phe-c(D-Cys-D-Trp-Lys-D-Cys)-Gaba-Tyr-NH$_2$;
Pip-Phe-c(D-Cys-D-Trp-Lys-D-Cys)-NH$_2$;
Pip-Phe-c(Cys-D-Trp-Lys-Cys)-Gaba-NH$_2$; or
Pro-Phe-c(D-Cys-D-Trp-Lys-D-Cys)-Thr-NH$_2$;
or a pharmaceutically acceptable salt thereof.

13. A compound according to claim 5, wherein said compound is according to the formula;
Phe-cyclo(Cys-D-Trp-Lys-Cys)-Thr-NH$_2$;
Phe-Tyr-cyclo(D-Cys-D-Trp-Lys-Cys)-Abu-Thr-NH$_2$;
Ac-D-Phe-Tyr-cyclo(D-Cys-D-Trp-Lys-Cys)-Abu-Thr-NH$_2$;
Nal-Tyr-cyclo(Cys-D-Trp-Lys-D-Cys)-Val-Nal-NH$_2$;
Nal-Tyr-cyclo(Cys-D-Trp-Lys-D-Cys)-Abu-Nal-NH$_2$;
Dip-Tyr-cyclo(D-Cys-D-Trp-Lys-D-Cys)-Abu-Nal-NH$_2$;
Nal-Tyr-cyclo(D-Cys-D-Trp-Lys-D-Cys)-Abu-Nal-NH$_2$;
Dip-Tyr-cyclo(D-Cys-D-Trp-Lys-D-Cys)-Val-Nal-NH$_2$;
Nal-Tyr-cyclo(D-Cys-D-Trp-Lys-D-Cys)-Val-Nal-NH$_2$;
Cpa-Pal-cyclo(D-Cys-D-Trp-Lys-D-Cys)-A3c-Nal-NH$_2$;
Cpa-Pal-cyclo(D-Cys-D-Trp-Lys-D-Cys)-A5c-Nal-NH$_2$;
Cpa-Pal-cyclo(D-Cys-D-Trp-Lys-D-Cys)-A6c-Nal-NH$_2$;
(G(z))aeg-cyclo(D-Cys-D-Trp-Lys-D-Cys)-A5c-Nal-NH$_2$;
D-Cpa-cyclo(Cys-D-Trp-Lys-D-Cys)-A5c-Nal-NH$_2$;
Pal-cyclo(D-Cys-D-Trp-Lys-D-Cys)-A5c-Nal-NH$_2$;
Cpa-cyclo(D-Cys-D-Trp-Lys-D-Cys)-A5c-Nal-NH$_2$;
Cpa-Pal-cyclo(D-Cys-D-Trp-Lys-D-Cys)-β-Ala-Nal-NH$_2$;
Cpa-Pal-cyclo(D-Cys-D-Trp-Lys-D-Cys)-Sar-Nal-NH$_2$;
Cpa-Pal-cyclo(D-Cys-D-Trp-Lys-D-Cys)-Aic-Nal-NH$_2$;
Cpa-Pal-cyclo(D-Cys-D-Trp-Lys-D-Cys)-Gaba-Nal-NH$_2$;
Cpa-Pal-cyclo(D-Cys-D-Trp-Lys-D-Cys)-Pro-Nal-NH$_2$;
(T)aeg-cyclo(D-Cys-D-Trp-Lys-D-Cys)-(A)aeg-NH$_2$;
Cpa-Pal-cyclo(D-Cys-D-Trp-Lys-D-Cys)-A4c-Nal-NH$_2$;
Cpa-Pal-cyclo(D-Cys-D-Trp-Lys-D-Cys)-Nal-NH$_2$;
Pal-cyclo(D-Cys-D-Trp-Lys-D-Cys)-Nal-NH$_2$;
Pro-Phe-cyclo(Cys-D-Trp-Lys-D-Cys)-Val-NH$_2$;
Pro-Phe-cyclo(D-Cys-D-Trp-Lys-D-Cys)-Val-NH$_2$;
Pip-4-NO$_2$-Phe-cyclo(D-Cys-D-Trp-Lys-D-Cys)-Nle-NH$_2$;
(G)aeg-Pal-cyclo(D-Cys-D-Trp-Lys-D-Cys)-Thr(Bzl)-(C)aeg-NH$_2$; or
(C)aeg-Pal-cyclo(D-Cys-D-Trp-Lys-D-Cys)-Thr(Bzl)-(G)aeg-NH$_2$;
or a pharmaceutically acceptable salt thereof.

14. A compound according to claim 7, wherein said compound is according to the formula
Nal-cyclo(D-Cys-Tyr-D-Trp-Lys-Cys)-Nal-NH$_2$;
D-Nal-cyclo(D-Cys-Tyr-D-Trp-Lys-Cys)-Nal-NH$_2$;
D-Phe-cyclo(Cys-Tyr-D-Trp-Lys-Cys)-Thr-NH$_2$;
D-4-NO$_2$-Phe-cyclo(D-Cys-Tyr-D-Trp-Lys-Cys)-Nal-NH$_2$;
Ac-D-4-NO$_2$-Phe-cyclo(D-Cys-Tyr-D-Trp-Lys-Cys)-Nal-NH$_2$;
D-4-NO$_2$-Phe-Pal-cyclo(D-Cys-Phe(4-O-Bzl)-D-Trp-Lys-Cys)-Tyr-NH$_2$;
Cpa-cyclo(D-Cys-Pal-D-Trp-Lys-Cys)-Thr(Bzl)-Tyr-NH$_2$;
D-4-NO$_2$-Phe-cyclo(D-Cys-Pal-D-Trp-Lys-Cys)-Thr-Tyr-NH$_2$;
D-4-NO$_2$-Phe-cyclo(D-Cys-Pal-D-Trp-Lys-Cys)-Thr(Bzl)-NH$_2$;
D-4-NO$_2$-Phe-cyclo(D-Cys-Pal-D-Trp-Lys-D-Cys)-Thr(Bzl)-Tyr-NH$_2$;
D-4-NO$_2$-Phe-cyclo(D-Cys-Tyr-D-Trp-Lys-Cys)-Thr(Bzl)-Tyr-NH$_2$;
4-NO$_2$-Phe-cyclo(D-Cys-Pal-D-Trp-Lys-Cys)-Thr(Bzl)-Tyr-NH$_2$;
D-Nal-cyclo(D-Cys-Pal-D-Trp-Lys-Cys)-Thr(Bzl)-Tyr-NH$_2$;
Pro-cyclo(D-Cys-Pal-D-Trp-Lys-Cys)-Thr(Bzl)-Tyr-NH$_2$;
Cpa-cyclo(D-Cys-Pal-D-Trp-Lys-Cys)-Thr(Bzl)-Nal-NH$_2$;
Ser(Bzl)-cyclo(D-Cys-Pal-D-Trp-Lys-Cys)-Thr-Tyr-NH$_2$;
(T)aeg-cyclo(D-Cys-Pal-D-Trp-Lys-D-Cys)-Thr(Bzl)-Tyr-NH$_2$;
(A)aeg-cyclo(D-Cys-Pal-D-Trp-Lys-Cys)-Thr(Bzl)-Tyr-NH$_2$;
(G)aeg-cyclo(D-Cys-Pal-D-Trp-Lys-Cys)-Thr(Bzl)-Tyr-NH$_2$;
(T)aeg-cyclo(D-Cys-4-Pal-D-Trp-Lys-Cys)-Thr(Bzl)-Tyr-NH$_2$;
(T)aeg-cyclo(D-Cys-Tyr-D-Trp-Lys-Cys)-Thr(Bzl)-Tyr-NH$_2$;
(T)aeg-cyclo(D-Cys-Phe-D-Trp-Lys-Cys)-Thr(Bzl)-Tyr-NH$_2$;
(T)aeg-cyclo(D-Cys-(T)aeg-D-Trp-Lys-Cys)-Thr(BZl)-Tyr-NH$_2$;
(T)aeg-cyclo(D-Cys-Pal-D-Trp-Lys-Cys)-Ser(Bzl)-Tyr-NH$_2$;
(T)aeg-cyclo(D-Cys-Pal-D-Trp-Lys-Cys)-Phe(4-O-Bzl)-Tyr-NH$_2$;
(T)aeg-cyclo(D-Cys-Pal-D-Trp-Lys-Cys)-A5c-Tyr-NH$_2$;
(T)aeg-cyclo(D-Cys-Pal-D-Trp-Lys-Cys)-Abu-Tyr-NH$_2$;
D-Cpa-cyclo(D-Cys-(T)aeg-D-Trp-Lys-Cys)-Thr(Bzl)-Tyr-NH$_2$;
(C)aeg-c(D-Cys-Pal-D-Trp-Lys-D-Cys)-Thr(Bzl)-Tyr-NH$_2$;
D-Cpa-c(D-Cys-Pal-D-Trp-Lys-D-Cys)Thr(Bzl)-Tyr-NH$_2$;
(T)aeg-c(Pen-Pal-D-Trp-Lys-D-Cys)Thr(Bzl)-Tyr-NH$_2$;
(T)aeg-c(D-Cys-Trp-D-Trp-Lys-D-Cys)Thr(Bzl)-Tyr-NH$_2$;
(T)aeg-c(D-Cys-Phe-D-Trp-Lys-D-Cys)Thr(Bzl)-Tyr-NH$_2$;
(T)aeg-c(D-Cys-Pal-D-Trp-Orn-D-Cys)Thr(Bzl)-Tyr-NH$_2$;
(T)aeg-c(D-Cys-Pal-D-Trp-hLys-D-Cys)Thr(Bzl)-Tyr-NH$_2$;
(T)aeg-c(D-Cys-Pal-D-Trp-Iamp-D-Cys)Thr(Bzl)-Tyr-NH$_2$;
(T)aeg-c(D-Cys-Pal-D-Trp-Cha(4-am)-D-Cys)Thr(Bzl)-Tyr-NH$_2$;
(T)aeg-c(D-Cys-Pal-D-Trp-Lys-D-Cys)-Ser(Bzl)-Tyr-NH$_2$;
(T)aeg-c(D-Cys-Pal-D-Trp-Lys-D-Cys)Thr(Bzl)-D-Tyr-NH$_2$;
(T)aeg-c(D-Cys-Pal-D-Trp-Lys-D-Cys)Thr(Bzl)-Trp-NH$_2$;
(T)aeg-c(D-Cys-Pal-D-Trp-Lys-D-Pen)Thr(Bzl)-Tyr-NH$_2$;
(C)aeg-c(D-Cys-Phe-D-Trp-Lys-D-Cys)Thr(Bzl)-Tyr-NH$_2$;
Ina-c(D-Cys-Phe-D-Trp-Lys-D-Cys)-Thr(Bzl)-Tyr-NH$_2$;
Mnf-c(D-Cys-Phe-D-Trp-Lys-D-Cys)-Thr(Bzl)-Tyr-NH$_2$;
Inp-c(D-Cys-Phe-D-Trp-Lys-D-Cys)-Thr(Bzl)-Tyr-NH$_2$;
Nua-c(D-Cys-Phe-D-Trp-Lys-D-Cys)-Thr(Bzl)-Tyr-NH$_2$;
(T)aeg-Pal-c(D-Cys-D-Trp-Lys-D-Cys)Thr(Bzl)-Tyr-NH$_2$;
(T)aeg-Pal-c(D-Cys-D-Trp-Lys-D-Cys)Tyr(Bzl)-Thr-NH$_2$;
(C)aeg-Phe-c(D-Cys-D-Trp-Lys-D-Cys)Thr(Bzl)-Tyr-NH$_2$; or
(T)aeg-D-Trp-c(D-Cys-Pal-Lys-D-Cys)Thr(Bzl)-Leu-NH$_2$;
or a pharmaceutically acceptable salt thereof.

15. A compound according to claim 7, wherein said compound is according to the formula
Hca-cyclo(D-Cys-Tyr-D-Trp-Lys-Cys)-Nal-NH$_2$;
Ac-Nal-cyclo(D-Cys-Tyr-D-Trp-Lys-Cys)-Nal-NH$_2$;
Ac-D-Phe-cyclo(D-Cys-Tyr-D-Trp-Lys-Cys)-Nal-NH$_2$;
Ac-D-Nal-cyclo(D-Cys-Tyr-D-Trp-Lys-Cys)-Nal-NH$_2$;
D-Phe-cyclo(D-Cys-Tyr-D-Trp-Lys-Cys)-Nal-NH$_2$;
Nal-cyclo(D-Cys-Tyr-D-Trp-Lys-Cys)-Nal-NH$_2$;
D-Nal-cyclo(D-Cys-Tyr-D-Trp-Lys-Cys)-Nal-NH$_2$;
D-Phe-cyclo(Cys-Tyr-D-Trp-Lys-Cys)-Thr-NH$_2$;
D-4-NO$_2$-Phe-Pal cyclo(D-Cys--Tyr-D-Trp-Lys-Cys)-Nal-NH$_2$;
Ac-D-4-NO$_2$-Phe-cyclo(D-Cys-Tyr-D-Trp-Lys-Cys)-Nal-NH$_2$;
D-4-NO$_2$-Phe-Pal-cyclo(D-Cys-Phe(4-O-Bzl)-D-Trp-Lys-Cys)-Tyr-NH$_2$
D-4-NO$_2$-Phe-cyclo(D-Cys-Pal-D-Trp-Lys-Cys)-Thr(Bzl)-Tyr-NH$_2$ Cpa-cyclo(D-Cys-Pal-D-Trp-Lys-Cys)-Thr(Bzl)-TYr-NH$_2$;

D-4-NO₂-Phe-cyclo(D-Cys-Pal-D-Trp-Lys-Cys)-Thr(Bzl)ᵣ-NH₂;
D-4-NO₂-Phe-cyclo(D-Cys-Pal-D-Trp-Lys-D-Cys)-Thr(Bzl)-Tyr-NH₂;
D-4-NO₂-Phe-cyclo(D-Cys-Tyr-D-Trp-Lys-Cys)-Thr(Bzl)-Tyr-NH₂;
4-NO₂-Phe-cyclo(D-Cys-Pal-D-Trp-Lys-Cys)-Thr(Bzl)-Tyr-NH₂;
D-Nal-cyclo(D-Cys-Pal-D-Trp-Lys-Cys)-Thr(Bzl)-Tyr-NH₂;
Pro-cyclo(D-Cys-Pal-D-Trp-Lys-Cys)-Thr(Bzl)-Tyr-NH₂;
Cpa-cyclo(D-Cys-Pal-D-Trp-Lys-Cys)-Thr(Bzl)-Nal-NH₂;
Ser(Bzl)-cyclo(D-Cys-Pal-D-Trp-Lys-Cys)-Thr-Tyr-NH₂;
(T)aeg-cyclo(D-Cys-Pal-D-Trp-Lys-Cys)-Thr(Bzl)-Tyr-NH₂;
(C)aeg-cyclo(D-Cys-Pal-D-Trp-Lys-Cys)-Thr(Bzl)-Tyr-NH₂;
Aic-cyclo(D-Cys-Pal-D-Trp-Lys-Cys)-Thr(Bzl)-Tyr-NH₂;
(C(z))aeg-cyclo(D-Cys-Pal-D-Trp-Lys-Cys)-Thr(Bzl)-Tyr-NH₂;
(A(z))aeg-cyclo(D-Cys-Pal-D-Trp-Lys-Cys)-Thr(Bzl)-Tyr-NH₂;
(T)aeg-cyclo(D-Cys-Pal-D-Trp-Lys-D-Cys)-Thr(Bzl)-Tyr-NH₂;
(A)aeg-cyclo(D-Cys-Pal-D-Trp-Lys-Cys)-Thr(Bzl)-Tyr-NH₂;
(G)aeg-cyclo(D-Cys-Pal-D-Trp-Lys-Cys)-Thr(Bzl)-Tyr-NH₂;
(T)aeg-cyclo(D-Cys-4-Pal-D-Trp-Lys-Cys)-Thr(Bzl)-Tyr-NH₂;
(T)aeg-cyclo(D-Cys-Tyr-D-Trp-Lys-Cys)-Thr(Bzl)-Tyr-NH₂;
(T)aeg-cyclo(D-Cys-Phe-D-Trp-Lys-Cys)-Thr(Bzl)-Tyr-NH₂;
(T)aeg-cyclo(D-Cys-(T)aeg-D-Trp-Lys-Cys)-Thr(Bzl)-Tyr-NH₂;
(T)aeg-cyclo(D-Cys-Pal-D-Trp-Lys-Cys)-Ser(Bzl)-Tyr-NH₂;
(T)aeg-cyclo(D-Cys-Pal-D-Trp-Lys-Cys)-Phe(4-O-Bzl)-Tyr-NH₂;
(T)aeg-cyclo(D-Cys-Pal-D-Trp-Lys-Cys)-ASc-Tyr-NH₂;
(T)aeg-cyclo(D-Cys-Pal-D-Trp-Lys-Cys)-Abu-Tyr-NH₂;
D-Cpa-cyclo(D-Cys-(T)aeg-D-Trp-Lys-Cys)-Thr(Bzl)-Tyr-NH₂;
(T)aeg-cyclo(D-Cys-Pal-D-Trp-Lys-D-Cys)-Thr(Bzl)-p-Me-Phe-NH₂;
Ac-(T)aeg-cyclo(D-Cys-Pal-D-Trp-Lys-D-Cys)-Thr(Bzl)-Tyr-NH₂;
(T)aeg-cyclo(D-Cys-Pal-D-Trp-Lys-D-Cys)-Nal-NH₂;
D-Cpa-cyclo(D-Cys-Pal-D-Trp-Lys-D-Cys)-Nal-NH₂;
(A)aeg-cyclo(D-Cys-Pal-D-Trp-Lys-D-Cys)-Thr(Bzl)-Tyr-NH₂;
(C)aeg-cyclo(D-Cys-Pal-D-Trp-Lys-D-Cys)-Thr(Bzl)-Tyr-NH₂;
(C)aeg-c(D-Cys-Pal-D-Trp-Lys-D-Cys)-Thr(Bzl)-Tyr-NH₂;
D-Cpa-c(D-Cys-Pal-D-Trp-Lys-D-Cys)Thr(Bzl)-Tyr-NH₂;
(T)aeg-c(Pen-Pal-D-Trp-Lys-D-Cys)Thr(Bzl)-Tyr-NH₂;
(T)aeg-c(D-Cys-Trp-D-Trp-Lys-D-Cys)Thr(Bzl)-Tyr-NH₂;
(T)aeg-c(D-Cys-Phe-D-Trp-Lys-D-Cys)Thr(Bzl)-Tyr-NH₂;
(T)aeg-c(D-Cys-Pal-D-Trp-Orn-D-Cys)Thr(Bzl)-Tyr-NH₂;
(T)aeg-c(D-Cys-Pal-D-Trp-hLys-D-Cys)Thr(Bzl)-Tyr-NH₂;
(T)aeg-c(D-Cys-Pal-D-Trp-Iamp-D-Cys)Thr(Bzl)-Tyr-NH₂;
(T)aeg-c(D-Cys-Pal-D-Trp-Cha(4-am)-D-Cys)Thr(Bzl)-Tyr-NH₂;
(T)aeg-c(D-Cys-Pal-D-Trp-Lys-D-Cys)-Ser(Bzl)-Tyr-NH₂;
(T)aeg-c(D-Cys-Pal-D-Trp-Lys-D-Cys)Thr(Bzl)-D-Tyr-NH₂;
(T)aeg-c(D-Cys-Pal-D-Trp-Lys-D-Cys)Thr(Bzl)-Trp-NH₂;
(T)aeg-c(D-Cys-Pal-D-Trp-Lys-D-Pen)Thr(Bzl)-Tyr-NH₂;
(C)aeg-c(D-Cys-Phe-D-Trp-Lys-D-Cys)Thr(Bzl)-Tyr-NH₂;
Ina-c(D-Cys-Phe-D-Trp-Lys-D-Cys)-Thr(Bzl)-Tyr-NH₂;
Mnf-c(D-Cys-Phe-D-Trp-Lys-D-Cys)-Thr(Bzl)-Tyr-NH₂;
Inp-c(D-Cys-Phe-D-Trp-Lys-D-Cys)-Thr(Bzl)-Tyr-NH₂;
Nua-c(D-Cys-Phe-D-Trp-Lys-D-Cys)-Thr(Bzl)-Tyr-NH₂;
(T)aeg-Pal-c(D-Cys-D-Trp-Lys-D-Cys)Thr(Bzl)-Tyr-NH₂;
(T)aeg-Pal-c(D-Cys-D-Trp-Lys-D-Cys)Tyr(Bzl)-Thr-NH₂;
(C)aeg-Phe-c(D-Cys-D-Trp-Lys-D-Cys)Thr(Bzl)-Tyr-NH₂; or
(T)aeg-D-Trp-c(D-Cys-Pal-Lys-D-Cys)Thr(Bzl)-Leu-NH₂;
or a pharmaceutically acceptable salt thereof.

16. A compound according to claim 9, wherein said compound is according to the formula
cyclo(Trp-D-Trp-Lys-Phe(4-O-Bzl)-Phe-(T)aeg);
cyclo(Trp-D-Trp-Lys-Pal-Phe-(T)aeg); or
cyclo(Phe-Phe-D-Trp-Lys-Thr-(T)aeg);
or a pharmaceutically acceptable salt thereof.

17. A method of eliciting a neuromedin B receptor agonist effect in a subject in need thereof, wherein said method comprises administering to said subject an effective amount of a compound according to claim 12, or a pharmaceutically acceptable salt thereof.

18. A method of eliciting a somatostatin receptor agonist effect in a subject in need thereof, wherein said method comprises administering to said subject an effective amount of a compound according to claim 13 or a pharmaceutically acceptable salt thereof.

19. A method of eliciting a neuromedin B receptor agonist effect in a subject in need thereof, wherein said method comprises administering to said subject an effective amount of a compound according to claim 14 or a pharmaceutically acceptable salt thereof.

20. A method of eliciting a somatostatin receptor agonist effect in a subject in need thereof, wherein said method comprises administering to said subject an effective amount of a compound according to claim 16 or a pharmaceutically acceptable salt thereof.

21. A method of eliciting a somatostatin receptor agonist effect in a subject in need thereof, wherein said method comprises administering to said subject an effective amount of a compound according to claim 16 or a pharmaceutically acceptable salt thereof, provided said compound is not cyclo(Trp-D-Trp-Lys-Phe(4-O-Bzl)-Phe-(T)aeg); or cyclo(Trp-D-Trp-Lys-Pal-Phe-(T)aeg).

22. A method of eliciting a SSTR-1 agonist effect in a subject in need thereof, wherein said method comprises administering to said subject an effective amount of a compound according to claim 14 or a pharmaceutically acceptable salt thereof, provided said compound is not
Nal-Tyr-cyclo(Cys-D-Trp-Lys-D-Cys)-Val-Nal-NH₂;
Nal-Tyr-cyclo(Cys-D-Trp-Lys-D-Cys)-Abu-Nal-NH₂;
Dip-Tyr-cyclo(D-Cys-D-Trp-Lys-D-Cys)-Abu-Nal-NH₂;
Nal-Tyr-cyclo(D-Cys-D-Trp-Lys-D-Cys)-Abu-Nal-NH₂;
Dip-Tyr-cyclo(D-Cys-D-Trp-Lys-D-Cys)-Val-Nal-NH₂;
Nal-Tyr-cyclo(D-Cys-D-Trp-Lys-D-Cys)-Val-Nal-NH₂;
Cpa-Pal-cyclo(D-Cys-D-Trp-Lys-D-Cys)-A3c-Nal-NH₂;
Cpa-Pal-cyclo(D-Cys-D-Trp-Lys-D-Cys)-A5c-Nal-NH₂;
Cpa-Pal-cyclo(D-Cys-D-Trp-Lys-D-Cys)-A6c-Nal-NH₂;
(G(z))aeg-cyclo(D-Cys-D-Trp-Lys-D-Cys)-A5c-Nal-NH₂;
D-Cpa-cyclo(Cys-D-Trp-Lys-D-Cys)-A5c-Nal-NH₂;
Pal-cyclo(D-Cys-D-Trp-Lys-D-Cys)-A5c-Nal-NH₂;
Cpa-cyclo(D-Cys-D-Trp-Lys-D-Cys)-A5c-Nal-NH₂;
Cpa-Pal-cyclo(D-Cys-D-Trp-Lys-D-Cys)-β-Ala-Nal-NH₂;
cyclo(D-Cys-D-Trp-Lys-D-Cys)-A5c-Nal-NH₂;
Cpa-Pal-cyclo(D-Cys-D-Trp-Lys-D-Cys)-Sar-Nal-NH₂;

Cpa-Pal-cyclo(D-Cys-D-Trp-Lys-D-Cys)-Aic-Nal-NH$_2$;
Cpa-Pal-cyclo(D-Cys-D-Trp-Lys-D-Cys)-Gaba-Nal-NH$_2$; or
Cpa-Pal-cyclo(D-Cys-D-Trp-Lys-D-Cys)-Pro-Nal-NH$_2$.

23. A method of eliciting a SSTR-1 agonist effect in a subject in need thereof, wherein said method comprises administering to said subject an effective amount of a compound according to claim 16 or a pharmaceutically acceptable salt thereof provided said compound is not
Ac-D-Phe-cyclo(D-Cys-Tyr-D-Trp-Lys-Cys)-Nal-NH$_2$;
Ac-D-Nal-cyclo(D-Cys-Tyr-D-Trp-Lys-Cys)-Nal-NH$_2$;
D-Phe-cyclo(D-Cys-Tyr-D-Trp-Lys-Cys)-Nal-NH$_2$;
Nal-cyclo(D-Cys-Tyr-D-Trp-Lys-Cys)-Nal-NH$_2$;
D-Nal-cyclo(D-Cys-Tyr-D-Trp-Lys-Cys)-Nal-NH$_2$;
D-4-NO$_2$-Phe-cyclo(D-Cys-Pal-D-Trp-Lys-Cys)-Thr(Bzl)-Tyr-NH$_2$;
Cpa-cyclo(D-Cys-Pal-D-Trp-Lys-Cys)-Thr(Bzl)-Tyr-NH$_2$;
D-4-NO$_2$-Phe-cyclo(D-Cys-Pal-D-Trp-Lys-Cys)-Thr(Bzl)-NH$_2$;
  D-4-NO$_2$-Phe-cyclo(D-Cys-Pal-D-Trp-Lys-D-Cys)-Thr(Bzl)-Tyr-NH$_2$;
D-4-NO$_2$-Phe-cyclo(D-Cys-Tyr-D-Trp-Lys-Cys)-Thr(Bzl)-Tyr-NH$_2$;
4-NO$_2$-Phe-cyclo(D-Cys-Pal-D-Trp-Lys-Cys)-Thr(Bzl)-Tyr-NH$_2$;
D-Nal-cyclo(D-Cys-Pal-D-Trp-Lys-Cys)-Thr(Bzl)-Tyr-NH$_2$;
Pro-cyclo(D-Cys-Pal-D-Trp-Lys-Cys)-Thr(Bzl)-Tyr-NH$_2$;
Cpa-cyclo(D-Cys-Pal-D-Trp-Lys-Cys)-Thr(Bzl)-Nal-NH$_2$;
Ser(Bzl)-cyclo(D-Cys-Pal-D-Trp-Lys-Cys)-Thr-Tyr-NH$_2$;
(T)aeg-cyclo(D-Cys-Pal-D-Trp-Lys-Cys)-Thr(Bzl)-Tyr-NH$_2$;
(c)aeg-cyclo(D-Cys-Pal-D-Trp-Lys-Cys)-Thr(Bzl)-Tyr-NH$_2$;
Aic-cyclo(D-Cys-Pal-D-Trp-Lys-Cys)-Thr(Bzl)-Tyr-NH$_2$;
(T)aeg-cyclo(D-Cys-Pal-D-Trp-Lys-D-Cys)-Thr(Bzl)-Tyr-NH$_2$;
(A)aeg-cyclo(D-Cys-Pal-D-Trp-Lys-Cys)-Thr(Bzl)-Tyr-NH$_2$;
(G)aeg-cyclo(D-Cys-Pal-D-Trp-Lys-Cys)-Thr(Bzl)-Tyr-NH$_2$;
(T)aeg-cyclo(D-Cys-4-Pal-D-Trp-Lys-Cys)-Thr(Bzl)-Tyr-NH$_2$;
(T)aeg-cyclo(D-Cys-Tyr-D-Trp-Lys-Cys)-Thr(Bzl)-Tyr-NH$_2$;
(T)aeg-cyclo(D-Cys-Phe-D-Trp-Lys-Cys)-Thr(Bzl)-Tyr-NH$_2$;
(T)aeg-cyclo(D-Cys-(T)aeg-D-Trp-Lys-Cys)-Thr(Bzl)-Tyr-NH$_2$;
(T)aeg-cyclo(D-Cys-Pal-D-Trp-Lys-Cys)-Ser(Bzl)-Tyr-NH$_2$;
(T)aeg-cyclo(D-Cys-Pal-D-Trp-Lys-Cys)-Phe(4-O-Bzl)-Tyr-NH$_2$;
(T)aeg-cyclo(D-Cys-Pal-D-Trp-Lys-Cys)-A5c-Tyr-NH$_2$;
(T)aeg-cyclo(D-Cys-Pal-D-Trp-Lys-Cys)-Abu-Tyr-NH$_2$; or
D-Cpa-cyclo(D-Cys-(T)aeg-D-Trp-Lys-Cys)-Thr(Bzl)-Tyr-NH$_2$.

24. A pharmaceutical composition comprising an effective amount of a compound according to claim 1, 2 or 3 or a pharmaceutically acceptable salt thereof and a pharmaceutically acceptable carrier to treat a medical condition or disease in a subject wherein said medical condition or disease is from the list consisting of lung cancer, glioma, anorexia, hypothyroidism, hyperaldosteronism, *H. pylori* proliferation, acromegaly, restenosis, Crohn's disease, systemic sclerosis, external and internal pancreatic pseudocysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux, Cushing's Syndrome, gonadotropinoma, hyperparathyroidism, Graves' Disease, diabetic neuropathy, Paget's disease, polycystic ovary disease, thyroid cancer, hepatome, leukemia, meningioma, cancer cachexia, orthostatic hypotension, postprandial hypotension, panic attacks, GH secreting adenomas, TSH secreting adenomas, prolactin secreting adenomas, insulinoma, glucagonoma, diabetes mellitus, hyperlipidemia, insulin insensitivity, Syndrome X, angiopathy, proliferative retinopathy, dawn phenomenon, Nephropathy, gastric acid secretion, peptic ulcers, enterocutaneous fistula, pancreaticocutaneous fistula, Dumping syndrome, watery diarrhea syndrome, pancreatitis, gastrointestinal hormone secreting tumor, angiogenesis, arthritis, allograft rejection, graft vessel bleeding, portal hypertension, gastrointestinal bleeding, obesity, and opioid overdose.

25. A method of treating a medical condition or disease in a subject, said method comprising administering to said subject a therapeutically effective amount of a compound of claim 1, 2 or 3, wherein said medical condition or disease is selected from the list consisting of lung cancer, glioma, anorexia, hypothyroidism, hyperaldosteronism, *H. pylori* proliferation, acromegaly, restenosis, Crohn's disease, systemic sclerosis, external and internal pancreatic pseudoCysts and ascites, VIPoma, nesidoblastosis, hyperinsulinism, gastrinoma, Zollinger-Ellison Syndrome, diarrhea, AIDS related diarrhea, chemotherapy related diarrhea, scleroderma, Irritable Bowel Syndrome, pancreatitis, small bowel obstruction, gastroesophageal reflux, duodenogastric reflux, Cushing's Syndrome, gonadotropinoma, hyperparathyroidism, Graves' Disease, diabetic neuropathy, Paget's disease, polycystic ovary disease, thyroid cancer, hepatome, leukemia, meningioma, cancer cachexia, orthostatic hypotension, postprandial hypotension, panic attacks, GH secreting adenomas, TSH secreting adenomas, prolactin secreting adenomas, insulinoma, glucagonoma, diabetes mellitus, hyperlipidemia, insulin insensitivity, Syndrome X, angiopathy, proliferative retinopathy, dawn phenomenon, Nephropathy, gastric acid secretion, peptic ulcers, enterocutaneous fistula, pancreaticocutaneous fistula, Dumping syndrome, watery diarrhea syndrome, pancreatitis, gastrointestinal hormone secreting tumor, angiogenesis, arthritis, allograft rejection, graft vessel bleeding, portal hypertension, gastrointestinal bleeding, obesity, and opioid overdose.

* * * * *